US011946164B2

(12) United States Patent
    Xie

(10) Patent No.: US 11,946,164 B2
(45) Date of Patent: *Apr. 2, 2024

(54) NANOFIBER STRUCTURES AND METHODS OF USE THEREOF

(71) Applicant: BOARD OF REGENTS OF THE UNIVERSITY OF NEBRASKA, Lincoln, NE (US)

(72) Inventor: Jingwei Xie, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/868,519

(22) Filed: Jul. 19, 2022

(65) Prior Publication Data

US 2022/0364269 A1    Nov. 17, 2022

Related U.S. Application Data

(63) Continuation of application No. 16/647,690, filed as application No. PCT/US2018/051716 on Sep. 19, 2018, now Pat. No. 11,427,936.

(60) Provisional application No. 62/560,314, filed on Sep. 19, 2017.

(51) Int. Cl.
| | |
|---|---|
| B29C 67/20 | (2006.01) |
| B29C 71/02 | (2006.01) |
| C08J 3/24 | (2006.01) |
| C08J 7/02 | (2006.01) |
| C08J 9/36 | (2006.01) |
| D01D 5/00 | (2006.01) |
| D01F 6/62 | (2006.01) |
| D01F 8/14 | (2006.01) |
| D04H 3/011 | (2012.01) |
| D06M 11/58 | (2006.01) |
| D06M 11/64 | (2006.01) |
| D06M 11/76 | (2006.01) |
| D06M 15/227 | (2006.01) |
| D06M 15/256 | (2006.01) |
| D06M 23/10 | (2006.01) |
| B29K 73/00 | (2006.01) |
| D06M 101/32 | (2006.01) |

(52) U.S. Cl.
CPC ......... *D01D 5/0007* (2013.01); *D01D 5/0015* (2013.01); *D01D 5/0023* (2013.01); *D01D 5/003* (2013.01); *D01D 5/0038* (2013.01); *D01D 5/0046* (2013.01); *D01F 6/625* (2013.01); *D01F 8/14* (2013.01); *D04H 3/011* (2013.01); *D06M 23/10* (2013.01); *B29C 2791/005* (2013.01); *B29C 2791/006* (2013.01); *B29K 2073/00* (2013.01); *D06M 2101/32* (2013.01)

(58) Field of Classification Search
CPC ... B29C 67/20; B29C 71/02; B29C 2791/005; B29C 2791/006; C08J 3/24; C08J 7/02; C08J 9/36; D01D 5/0038; D06M 7/00; D06M 11/58; D06M 11/64; D06M 11/76; D06M 15/227; D06M 15/256; D06M 23/10
USPC ... 264/51, 85, 101, 211, 236, 343, 347, 464, 264/465, 466, 484; 8/130.1; 521/94, 95, 521/97, 98
See application file for complete search history.

(56) References Cited

U.S. PATENT DOCUMENTS

| | | |
|---|---|---|
| 3,674,540 A | 7/1972 | Pergaminos |
| 6,653,005 B1 | 11/2003 | Muradov |
| 7,704,740 B2 | 4/2010 | Schindler et al. |
| 9,403,958 B2 | 8/2016 | Lindner et al. |
| 9,655,995 B2 | 5/2017 | Xie et al. |
| 9,913,862 B2 | 3/2018 | Collins et al. |
| 10,799,620 B2 | 10/2020 | Xie et al. |
| 11,033,659 B2 | 6/2021 | Xie et al. |
| 11,318,224 B2 | 5/2022 | Xie et al. |
| 2005/0084532 A1 | 4/2005 | Howdle et al. |
| 2005/0187330 A1 | 8/2005 | Gulari et al. |
| 2006/0002978 A1 | 1/2006 | Shea et al. |
| 2007/0077272 A1 | 4/2007 | Li et al. |
| 2008/0112998 A1 | 5/2008 | Wang |
| 2010/0183699 A1 | 7/2010 | Wan et al. |
| 2011/0070151 A1 | 3/2011 | Braithwaite et al. |
| 2011/0195123 A1 | 8/2011 | Shemi |
| 2011/0293685 A1 | 12/2011 | Kuo et al. |
| 2012/0040581 A1 | 2/2012 | Kim |
| 2012/0226295 A1 | 9/2012 | Jabbari |
| 2013/0095167 A1 | 4/2013 | Warnke |
| 2013/0112625 A1 | 5/2013 | Bahukudumbi et al. |
| 2014/0024760 A1 | 1/2014 | Kwon et al. |
| 2014/0051169 A1 | 2/2014 | Ganey et al. |
| 2016/0015792 A1 | 1/2016 | Hendricus Van Pinxteren et al. |
| 2016/0015952 A1 | 1/2016 | Omachi et al. |

(Continued)

FOREIGN PATENT DOCUMENTS

| | | |
|---|---|---|
| CN | 102068716 A | 5/2011 |
| CN | 102071485 A | 5/2011 |

(Continued)

OTHER PUBLICATIONS

Wei, et al., "The multifunctional wound dressing with core-shell structured fibers prepared by coaxial electrospinning" Front. Mater. Sci. (2016) 10(2):113-121.

(Continued)

*Primary Examiner* — Leo B Tentoni
(74) *Attorney, Agent, or Firm* — Robert C. Netter, Jr.; Dann, Dorfman, Herrell & Skillman

(57) ABSTRACT

Expanded, nanofiber structures are provided as well as methods of use thereof and methods of making.

20 Claims, 15 Drawing Sheets

(56) References Cited

U.S. PATENT DOCUMENTS

| | | |
|---|---|---|
| 2016/0106548 A1 | 4/2016 | Li et al. |
| 2016/0176714 A1 | 6/2016 | Do et al. |
| 2017/0296703 A1 | 10/2017 | Xie et al. |
| 2019/0209732 A1 | 7/2019 | Xie et al. |
| 2020/0164107 A1 | 5/2020 | Xie et al. |
| 2020/0277711 A1 | 9/2020 | Xie |
| 2021/0268154 A1 | 9/2021 | Xie et al. |
| 2022/0226537 A1 | 7/2022 | Xie et al. |

FOREIGN PATENT DOCUMENTS

| | | |
|---|---|---|
| CN | 102703996 A | 10/2012 |
| CN | 103382625 A | 11/2013 |
| CN | 104464712 A | 3/2015 |
| CN | 106421898 A | 2/2017 |
| CN | 106492289 A | 3/2017 |
| CN | 106563172 A | 4/2017 |
| CN | 106620881 A | 5/2017 |
| CN | 105012991 B | 1/2018 |
| EP | 1611877 A1 | 1/2006 |
| EP | 2813212 A1 | 12/2014 |
| JP | 2006-169497 A | 6/2006 |
| JP | 2007160691 A | 6/2007 |
| JP | 2007222477 A | 9/2007 |
| JP | 4656320 B2 | 3/2011 |
| KR | 101493444 B1 | 2/2015 |
| WO | 00/50104 A1 | 8/2000 |
| WO | 2006/019600 A2 | 2/2006 |
| WO | 2018/227078 A1 | 12/2008 |
| WO | 2009/011658 A1 | 1/2009 |
| WO | 2009/088777 A1 | 7/2009 |
| WO | 2014/037651 A1 | 3/2014 |
| WO | 2014/191739 A1 | 12/2014 |
| WO | 2015/051042 A2 | 4/2015 |
| WO | 2016/053988 A1 | 4/2016 |
| WO | 2018/064281 A1 | 4/2018 |
| WO | 2019209762 A1 | 10/2019 |

OTHER PUBLICATIONS

Chen, et al., "Fabrication of Injectable and Superelastic Nanofiber Rectangle Matrices ("Peanuts") and Their Potential Applications in Hemostasis" Biomaterials (2018) 179:46-59.

Liu, Y., et al., "HB-EGF embedded in PGA/PLLA scaffolds via subcritical CO2 augments the production of tissue engineered intestine" Biomaterials (2016) 103:150-159.

Geiger, B.C., et al., "Dual Drug Release from CO2-Infused Nanofibers via Hydrophobic and Hydrophilic Interactions" J. Appld. Polymer Sci. (2015) 132(38):42571.

Ayodeji, O., et al., "Carbon dioxide impregnation of electrospun polycaprolactone fibers" J. Supercritical Fluids (2007) 41:173-178.

Jiang, J., et al., "CO2-Expanded Nanofiber Scaffolds Maintain Activity of Encapsulated Bioactive Materials and Promote Cellular Infiltration and Positive Host Response" Acta Biomater. (2018) 68:237-248.

Nazarov, R., et al., "Porous 3-D scaffolds from regenerated silk fibroin" Biomacromolecules (2004) 5(3):718-26.

Joshi, M.K., et al., "Multi-layered macroporous three-dimensional nanofibrous scaffold via a novel gas foaming technique" Chem. Engr. J. (2015) 275:79-88.

Bencherif, S.A., et al., "Advances in the design of macroporous polymer scaffolds for potential applications in dentistry" J. Periodontal Implant Sci. (2013) 43(6):251-61.

Xie, J., et al., "Putting Electrospun Nanofibers to Work for Biomedical Research" Macromol. Rapid Commun. (2008) 29:1775-1792.

Jiang, J., et al., "Expanding Two-Dimensional Electrospun Nanofiber Membranes in the Third Dimension By a Modified Gas-Foaming Technique" ACS Biomater. Sci. Eng. (2015) 1(10):991-1001.

Liu, W., et al., "Electrospun nanofibers for regenerative medicine" Adv. Healthc. Mater. (2012) 1(1):10-25.

Nam, Y.S., et al., "A Novel Fabrication Method of Macroporous Biodegradable Polymer Scaffolds Using Gas Foaming Salt as a Porogen Additive" J. Biomed. Mater. Res. (2000) 53(1):1-7.

Lee, Y.H., et al., "Electrospun dual-porosity structure and biodegradation morphology of Montmorillonite reinforced PLLA nanocomposite scaffolds" Biomaterials (2005) 26:3165-3172.

Jiang, J., et al., "Local Sustained Delivery of 25-Hydroxyvitamin D3 for Production of Antimicrobial Peptides" Pharm. Res. (2015) 32(9): 2851-2862.

Ma, B., et al., "Rational design of nanofiber scaffolds for orthopedic tissue repair and regeneration" Nanomedicine (2013) 8(9):1459-81.

Dehghani, et al., "Engineering porous scaffolds using gas-based techniques" Current Opinion in Biotechnology (2011) 22:661-666.

Mulmi, et al., "Fabrication of Air Freshening Spongy Three Dimensional Electrospun Membrane" Journal of the Institute of Engineering (2018) 14(1):14-21.

Keit, et al., "Expansion of Two-dimension Electrospun Nanofiber Mats into Three-dimension Scaffolds" J. Vis. Exp. (2018):e58918.

Liu, Y., et al., "Composite vascular scaffold combining electrospun fibers and physically-crosslinked hydrogel with copper wire-induced grooves structure" J. Mech. Behav. Biomed. Mater. (2016) 61:12-25.

Zhao, Y., et al., "Preparation of Nanofibers with Renewable Polymers and Their Application in Wound Dressing" Intl. J. Polmer Sci. (2016) 2016:4672839.

Pok, S., et al., "A multilayered scaffold of a chitosan and gelatin hydrogel supported by a PCL core for cardiac tissue engineering" Acta Biomater. (2013) 9(3):5630-5642.

Xie, J, et al., "Controlled biomineralization of electrospun poly(E-caprolactone) fibers for enhancing their mechanical properties" Acta Biomaterialia (2013) 9(3):5698-5707.

Xie, J., et al., "The differentiation of embryonic stem cells seeded on electrospun nanofibers into neural lineages" Biomaterials (2009) 30(3):354-362.

Chen, S., et al.,. "Recent advances in electrospun nanofibers for wound healing" Nanomedicine (Lond.) (2017) 12(11):1335-1352.

Electrospin Tech, "Post-electrospinning expansion of 2D membrane to 3D scaffold using gas foaming" (Oct. 27, 2015) available at: http://electrospintech.com/gasfoam3d.html#.X5bnPC9h0kg.

Borjigin, M., et al., "Proliferation of Genetically Modified Human Cells on Electrospun Nanofiber Scaffolds" Mol. Ther.-Nuc. Acids (2012) 1:e59.

Lee, S.J., et al., "The use of thermal treatments to enhance the mechanical properties of electrospun poly(E-caprolactone) scaffolds" Biomaterials (2008) 29:1422-1430.

Xie, J., et al., "Electrospray in the dripping mode for cell microencapsulation" J. Colloid Interface Sci. (2007) 312:247-255.

Cai, H., et al., "Aerogel Microspheres from Natural Cellulose Nanofibrils and Their Application as Cell Culture Scaffold" Biomacromolecules (2014) 15:2540-2547.

Hwang, P.T.J., et al., "Poly(ε-caprolactone)/gelatin composite electrospun scaffolds with porous crater-like structures for tissue engineering" J Biomed Mater Res A. (2016) 104(4):1017-1029.

Wang, W., et al., "Dentin regeneration by stem cells of apical papilla on injectable nanofibrous microspheres and stimulated by controlled BMP-2 release" Acta Biomater. (2016) 36:63-72.

Gu, B.K., et al., "Fabrication of sonicated chitosan nanofiber mat with enlarged porosity for use as hemostatic materials" Carbohydr. Polym. (2013) 97(1):65-73.

Jiang, J., et al., "Expanded Three-dimensional Nanofiber Scaffolds: Cell Penetration, Neovascularization, and Host Response" Adv. Healthc. Mater. (2016) 5(23): 2993-3003.

Gao, Q., et al., "Fabrication of electrospun nanofibrous scaffolds with 3D controllable geometric shapes" Mater. Design (2018) 157:159-169.

Boda, S.K., et al., "Electrospraying Electrospun Nanofiber Segments into Injectable Microspheres for Potential Cell Delivery" ACS Appl. Mater. Interfaces (2018) 10:25069-25079.

Boda, S.K., et al., "Mineralized nanofiber segments coupled with calcium-binding BMP-2 peptides for alveolar bone regeneration" Acta Biomater. (2019) 85:282-293.

(56) References Cited

OTHER PUBLICATIONS

Fu, L., et al., "Three-dimensional nanofiber scaffolds with arrayed holes for engineering skin tissue constructs" MRS Communications (2017) 7:361-366.

Kang, et al., "Chitosan-coated poly(vinyl alcohol) nanofibers for wound dressings" J. Biomed. Mater. Res. B Appl. Biomater. (2010) 92(2):568-76.

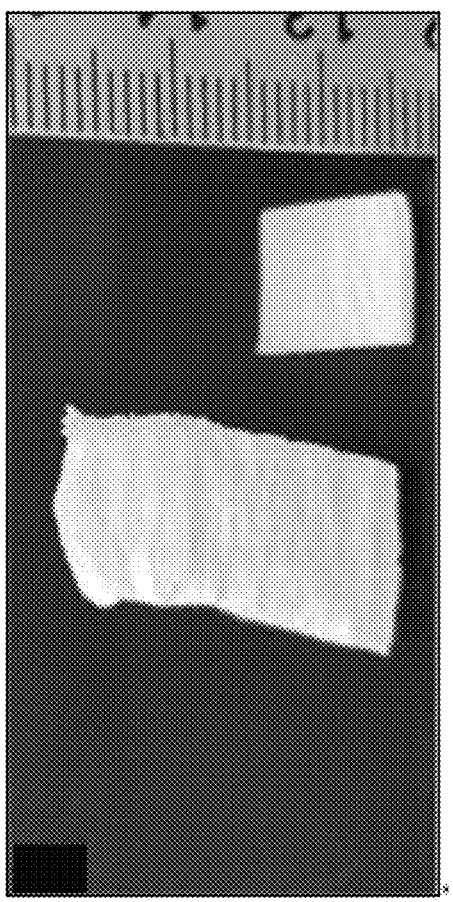
FIG. 1A
FIG. 1B
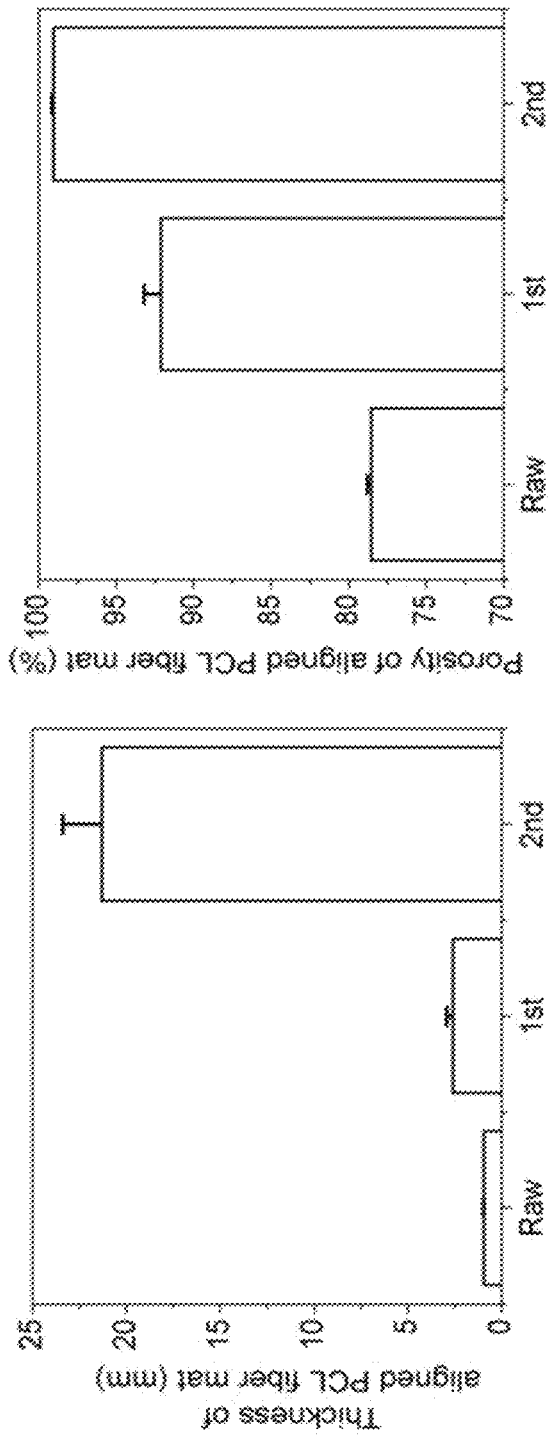
FIG. 1C
FIG. 1D

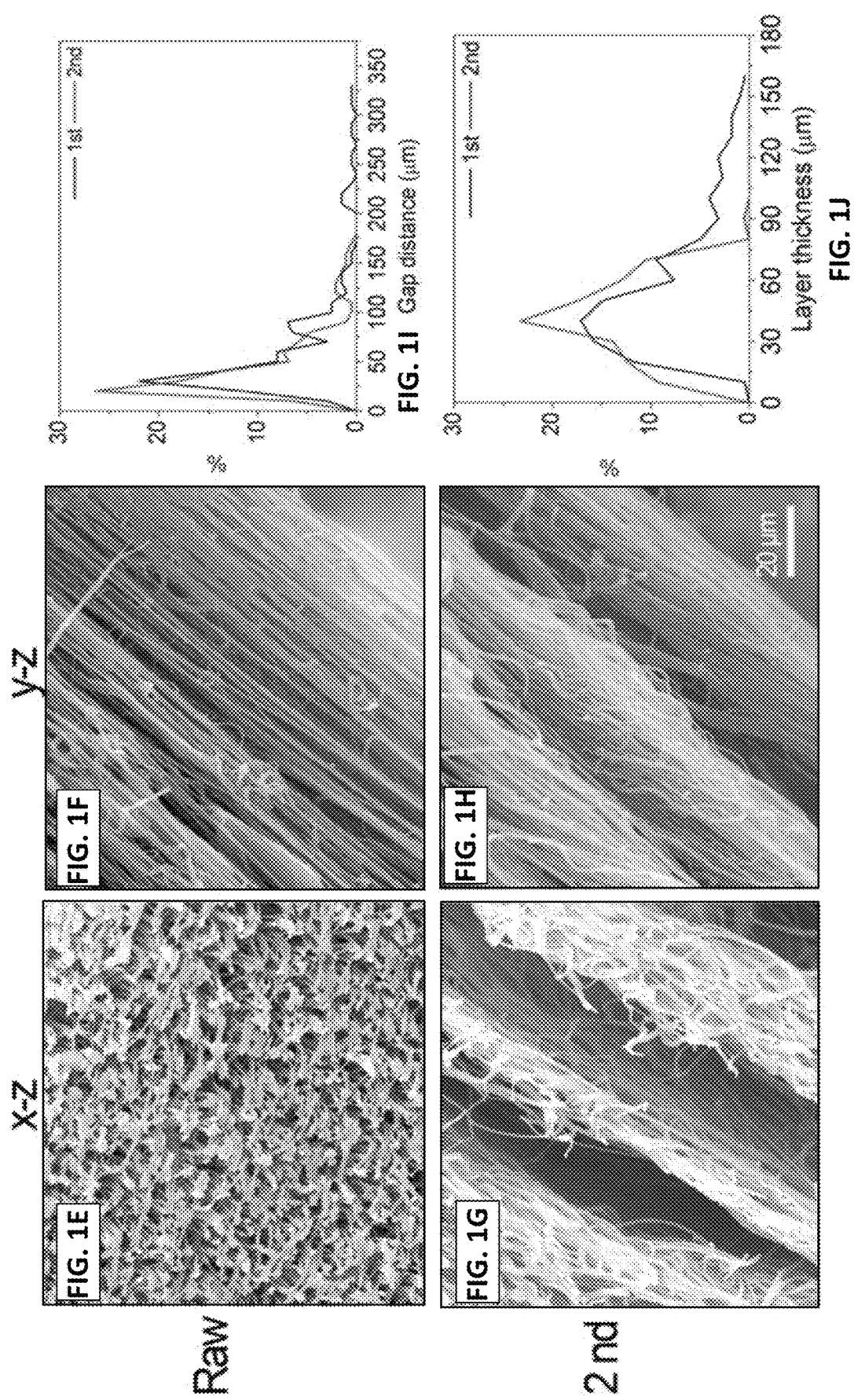

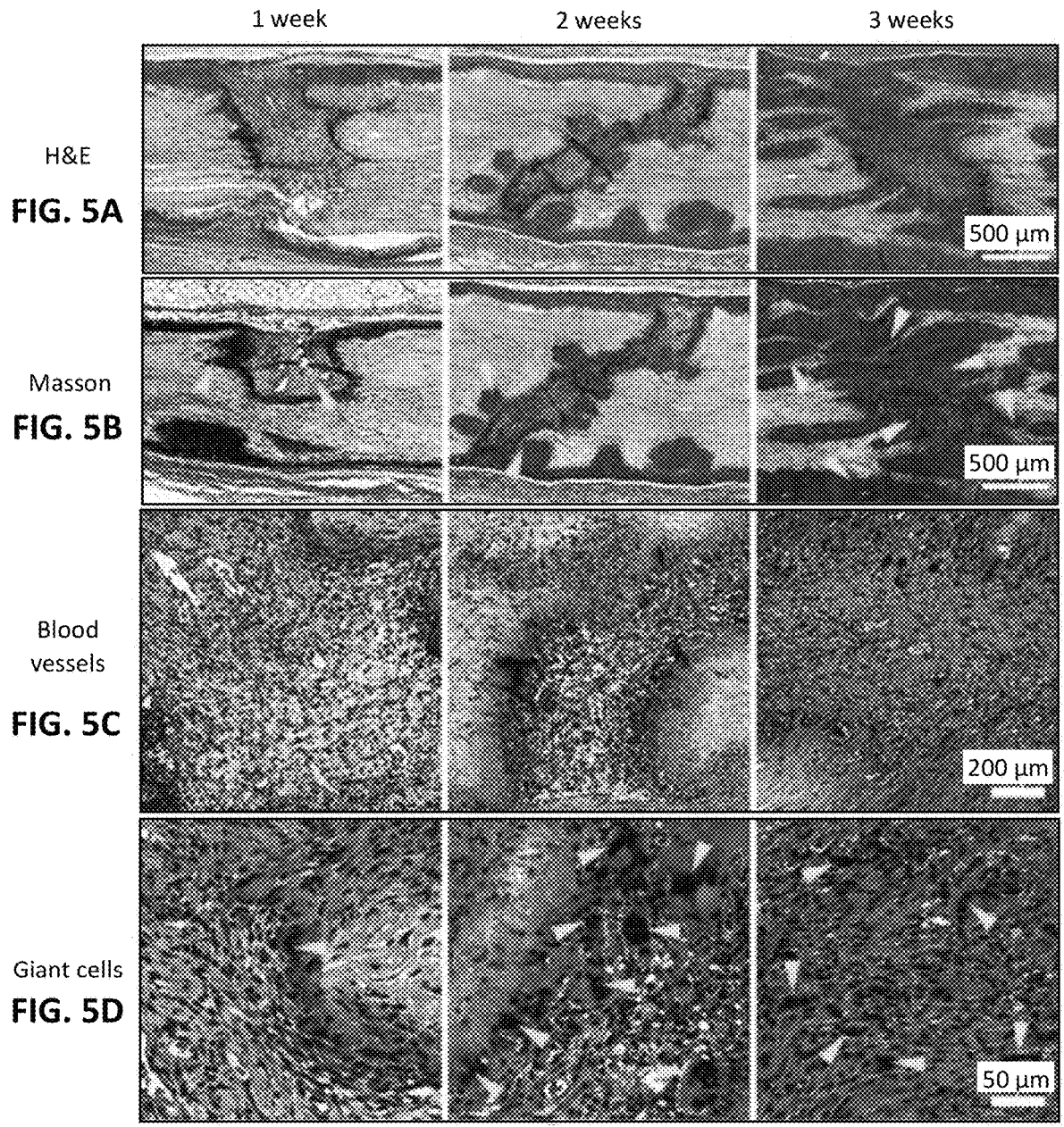

NANOFIBER STRUCTURES AND METHODS OF USE THEREOF

This application is a continuation application of U.S. patent application Ser. No. 16/647,690, filed Mar. 16, 2020, now U.S. Pat. No. 11,427,936, which is a § 371 application of PCT/US2018/051716, filed Sep. 19, 2018, which claims priority under 35 U.S.C. § 119(e) to U.S. Provisional Patent Application No. 62/560,314, filed Sep. 19, 2017. The foregoing applications are incorporated by reference herein.

This invention was made with government support under Grant No. R01 GM123081 awarded by the National Institutes of Health (NIH). The government has certain rights in the invention.

FIELD OF THE INVENTION

This application relates to the fields of nanofibers and nanofiber structures. More specifically, this invention provides methods of synthesizing nanofiber structures and methods of use thereof.

BACKGROUND OF THE INVENTION

Several publications and patent documents are cited throughout the specification in order to describe the state of the art to which this invention pertains. Each of these citations is incorporated herein by reference as though set forth in full.

Potential applications for electrospun nanofibers include energy storage, healthcare, biotechnology, environmental cleaning, defense and security (Ramakrishna, et al. (2006) Mater. Today 9:40-50; Sridhar, et al. (2015) Chem. Soc. Rev., 44:790-814; Xie, et al. (2008) Macromol. Rapid Commun., 29:1775-1792). Due to their ability to mimic the architecture of the extracellular matrix (ECM) and the size of collagen fibrils in ECM, electrospun nanofibers have been widely used as scaffolding materials for tissue repair and regeneration (Xie, et al. (2008) Macromol. Rapid Commun., 29:1775-1792; Xie, et al. (2010) Nanoscale 2:35-44; Xie, et al. (2010) Nanoscale 2:923-926; Kennedy, et al. (2017) Acta Biomater., 50:41-55; Liu, et al. (2012) Adv. Healthc. Mater., 1:10-25). One limiting factor of conventional electrospinning is that the produced nanofiber mats are composed entirely of densely packed nanofibers only providing a superficial porous structure during the process of the sheet-like assembly (Mahjour, et al. (2016) J. Biomed. Mater. Res. A, 104:1479-1488; Wu, et al. (2016) Bioactive Materials 1:56-64; Sun, et al. (2012) Nanoscale 4:2134-2137). Cells incubated with such a nanofiber mat normally results in the formation of a cell monolayer on its surface rather than a three-dimensional (3D) cellular construct throughout the mat (Kang, et al. (2016) Biofabrication 8:025008). The poor cellular penetration has been attributed to the reduced porosity of nanofiber mats, and the sizes of inter-fiber pores often smaller than the dimensions of individual cells (Mahjour, et al. (2016) J. Biomed. Mater. Res. A, 104:1479-1488). In addition, the reduced porosity could limit oxygen and nutrient transportation, further hindering cellular infiltration (Kim, et al. (2007) J. Biomed. Mater. Res. B Appl. Biomater., 81:104-110). Therefore, the unfavorable characteristic of conventional electrospun nanofiber mats mainly due to the intrinsic property of the electrospinning technique limits cellular infiltration and growth throughout the nanofiber mats. Clearly, there is a need for improved electrospun mats.

SUMMARY OF THE INVENTION

In accordance with the instant invention, nanofiber/nanofibrous structures are provided. In a particular embodiment, the nanofiber/nanofibrous structures comprise an expanded, nanofiber structure comprising a plurality of nanofibers. In a particular embodiment, the nanofiber structure has been expanded by exposure to a subcritical fluid such as subcritical $CO_2$ and then depressurized (e.g., within a container). The nanofiber structure may comprise a plurality of electrospun nanofibers (e.g., uniaxially-aligned, random, entangled, and/or electrospun fibers). The nanofiber structure may also comprise a material that enhances water absorption, such as gelatin, chitosan, or collagen. In a particular embodiment, the nanofiber structure is cross-linked. The nanofiber structure may also comprise one or more agents or compounds such as therapeutic agents. In a particular embodiment, the nanofiber structure comprises a plurality of holes, particularly an array of holes. In a particular embodiment, the holes of the nanofiber structure comprise cells and/or tissue. Methods of synthesizing the nanofiber structure of the instant invention are also provided.

In accordance with another aspect of the instant invention, methods of using the nanofiber structures are provided. For example, the nanofiber structures may be used to enhance wound healing, build tissue constructs, promote tissue regeneration, reduce, inhibit, prevent, and/or eliminate infection, local delivery of drugs, and/or inhibit bleeding.

BRIEF DESCRIPTION OF THE DRAWINGS

FIGS. 1A-1J show the expansion and characterization of aligned nanofiber scaffolds. FIG. 1A: Photographs of aligned PCL nanofiber mats after the first treatment of subcritical $CO_2$ fluid (left) and raw PCL nanofiber mats (right). FIG. 1B: Photographs of aligned PCL nanofiber mats after the second treatment (left) and raw PCL nanofiber mats (right). FIG. 1C: Thickness of aligned PCL fiber mats after expanding once and twice. FIG. 1D: The corresponding porosities of aligned PCL fiber mats after expanding once and twice. FIGS. 1E-1H: SEM images showing cross-sectional morphologies of aligned PCL fiber mats before (FIGS. 1E, 1F) expansion and after expansion in subcritical $CO_2$ fluid two times (FIGS. 1G, 1H). The scale bar is 20 µm.

FIG. 3A: Photograph showing $NaBH_4$ expanded PCL fiber mats with coumarin 6 loading ($NaBH_4$) and $CO_2$ expanded PCL fiber mats with coumarin 6 loading ($CO_2$) FIG. 3B: Top view of $CO_2$ liquid expanded PCL fiber mats with coumarin 6 loading (top left), $NaBH_4$ expanded PCL fiber mats with coumarin 6 loading (bottom left), PCL fiber mats with coumarin 6 loading (top right), and raw PCL fiber mats (bottom right). Insets: fluorescent images of each sample. FIG. 3C: The fluorescence intensity quantified by Image J software.

FIG. 4A: The in vitro release kinetics of LL 37 from expanded and unexpanded PCL fiber samples (Initial drug loading: 5 µg/mg). FIG. 4B: Antibacterial performance of different fiber samples. PCL: unexpanded pristine PCL nanofiber membranes. PCL-LL37: LL37-loaded PCL nanofiber scaffolds.

FIGS. 5A-5F show the in vivo response of expanded nanofiber scaffolds with arrayed holes and traditional nanofiber mats. FIG. 5A: H & E staining. Dots indicate the boundary of cell filtrated area. FIG. 5B: Masson's trichrome staining. Arrows indicate collagen deposition. FIG. 5C: Highly magnified images of FIG. 5A. FIG. 5D: Highly magnified images of FIG. 5A. Arrows indicate giant cells. FIG. 5E: Quantification of blood vessel formation per $mm^2$. FIG. 5F: Quantification of giant cells per implant.

DETAILED DESCRIPTION OF THE INVENTION

Figure 2B:
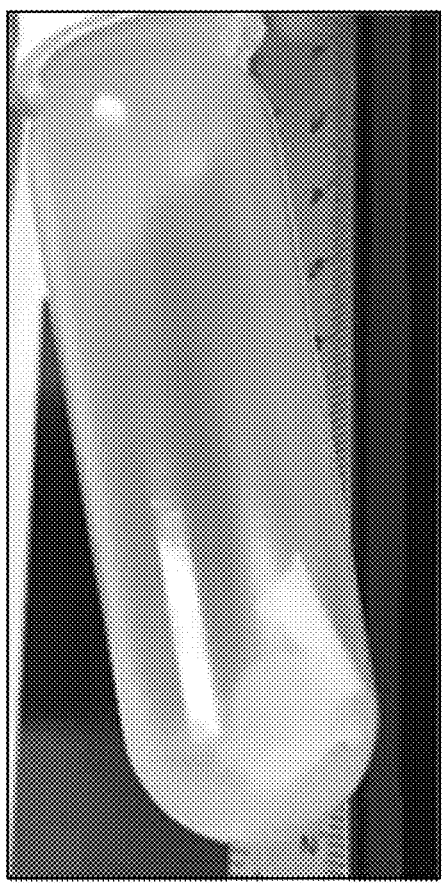
FIGS. 2A-2D provide photographs of poly(vinylpyrrolidone) (PVP) nanofiber mats before (FIGS. 2A, 2B) and after (FIGS. 2C, 2D) expansion in subcritical $CO_2$ fluid. Due to the high hydrophilicity of PVP nanofibers, expanded PVP membranes were kept in the capped tube to prevent dissolving from water condensed from the surrounding air (FIG. 2C). The expanded membrane was taken out after the temperature of samples reached the room temperature (FIG. 2D).
Figure 2A:
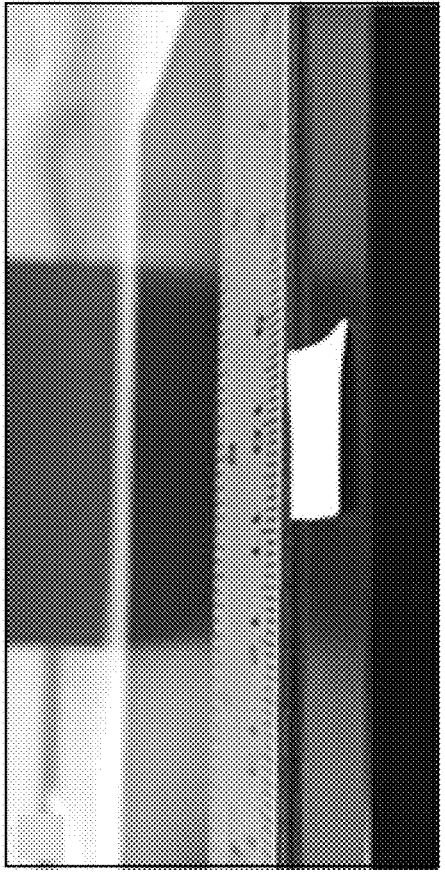
Figure 2D:
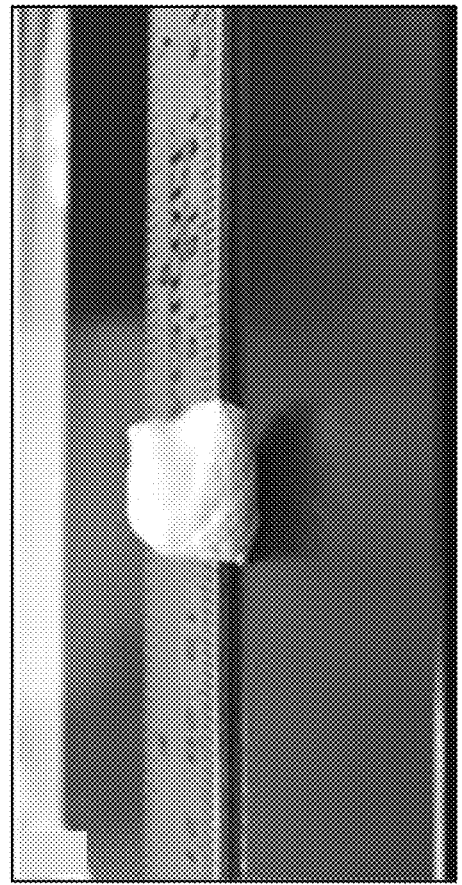
Figure 2C:
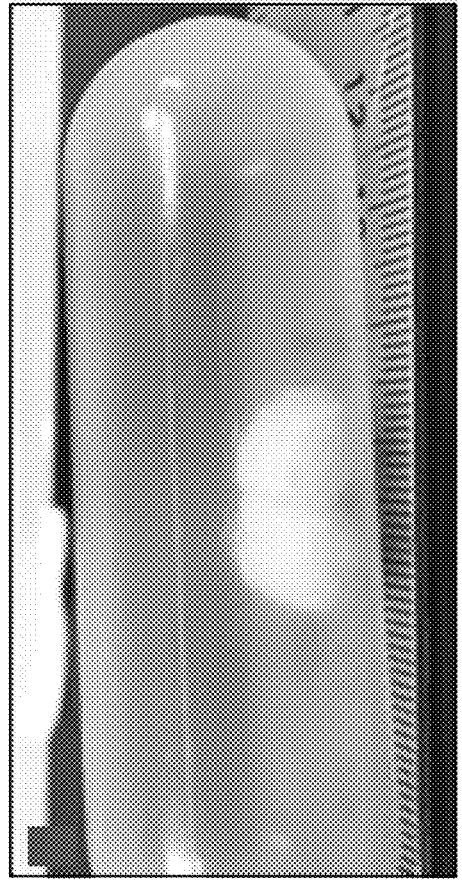

A number of methods have been attempted to overcome the obstacles that inhibit the use of nanofiber mats in regenerative medicine. To increase the pore size of electrospun nanofiber scaffolds, a simple and straightforward way is to modulate fiber diameters (Sell, et al. (2008) J. Biomed. Mater. Res. A, 85:115-126; Balguid, et al. (2009) Tissue Eng. Part A, 15:437-444; Fong, et al. (2013) Proc. Natl. Acad. Sci., 110:6500-6505; Pham, et al. (2006) Biomacromolecules 7:2796-2805). Studies show that the diameters of fibers larger than 4 µm could lead to the pore size larger than 20 µm (Pham, et al. (2006) Biomacromolecules 7:2796-2805). The issue for this method is that the fibers with a size in micron scale lack the biomimetic property and the interactions between microfibers and cells could be different from the interactions between nanofibers and cells. Manipulation of electric field with a modified collector during electrospinning was also used to generate 3D cotton-like fluffy nanofiber scaffolds (Blakeney, et al. (2011) Biomaterials 32:1583-1590). This approach was limited to the generation of scaffolds made of random nanofibers lacking nanotopographic cues and the difficulty in the control of porosity. Alternatively, ionic salts that were added to the electrospinning solution could manipulate the electrostatic repulsion between substrates and deposited nanofibers to fabricate sponge like nanofiber matrix (Jin, et al. (2015) Angew. Chem., 54:7587-7591). This approach only produced limited thickness of nanofiber matrix and necessitated the use of additives (e.g., ionic salts) that may cause side effects or safety issues during tissue regeneration. Another strategy to increase the porosity is selective removal of sacrificial fibers (Baker, et al. (2008) Biomaterials 29:2348-2358; Baker, et al. (2012) Proc. Natl. Acad. Sci., 109:14176-14181). This method only generated a limited increase of porosity. Based on the similar principle, ice crystals were used as sacrificial templates to fabricate 3D electrospun nanofiber scaffolds with large interconnected pores (Leong, et al. (2009) J. Biomed. Mater. Res. A, 91:231-240). Similarly, salt particles incorporated into electrospun nanofiber scaffolds during the electrospinning process resulted in the formation of macropores 100 µm after leaching (Nam, et al. (2007) Tissue Eng., 13:2249-2257). This strategy necessitates the removal of sacrificial templates involving multiple steps. As mentioned above, these approaches were associated with various issues including difficulty to control the thickness, limited to certain materials, restriction to randomly oriented nanofibers, the necessity of additives, time-consuming processing, need for aqueous solutions, insufficient expansion ratios, and/or multiple steps.

Electrospun nanofiber mats can be expanded in the third dimension with ordered structures using gas bubbles generated by chemical reactions in an aqueous solution (Jiang, et al. (2015) ACS Biomater. Sci. Eng., 1:991-1001; Jiang, et al. (2016) Adv. Healthcare Mater., 5:2993-3003; Joshi, et al. (2015) Chem. Eng. J., 275:79-88). Compared to previous approaches, this methodology overcame some of the above shortcomings and showed some improvement in the generation of 3D electrospun nanofiber scaffolds. Although expansion of nanofiber mats with cellular infiltration and proliferation occurring throughout the whole scaffolds (Jiang, et al. (2015) ACS Biomater. Sci. Eng., 1:991-1001; Jiang, et al. (2016) Adv. Healthcare Mater., 5:2993-3003), some issues still remained with the expansion procedure: i) it was a multi-step, time consuming process, involving gas production process in an aqueous solution followed by freeze-drying; ii) there was a risk that $NaBH_4$ could react with polymers or encapsulated substances; iii) there could be a loss of bioactive materials encapsulated in fibers; iv) there could be a loss of bioactivities for materials incorporated in the fibers; and v) the method was limited to water-insoluble materials.

Subcritical $CO_2$ fluid has been used in oil and fragrance extraction and in the processing of polymeric materials, because it is nontoxic, non-flammable, inexpensive, and environmentally friendly (Garland, et al. (2016) J. Essential Oil Res., 28:55-63; Taraj, et al. (2013) Asian J. Chem., 25:7361-7364; Rout, et al. (2008) J. Supercritical Fluids 45:200-205; Bhamidipati, et al. (2013) Mater. Sci. Eng. C Mater. Biol. Appl., 33: 4892-4899; Wang, et al. (2007) Cellular Polym., 26:11-35; Yang, et al. (2005) J. Vac. Sci. Tech. B, 23:3202). Herein, a simple and novel method for processing traditional electrospun poly(ε-caprolactone) (PCL) nanofiber mats from 2D to 3D by immersing fiber mats in subcritical $CO_2$ fluid followed by depressurization. $CO_2$ expanded 3D nanofiber scaffolds can have a similar structure as the ones generated using a gas production chemical reaction in an aqueous solution. $CO_2$ expanded 3D nanofiber scaffolds can also better maintain the activity of encapsulated bioactive materials compared to previous approaches due to the low-temperature process. In addition, $CO_2$ expanded 3D nanofiber scaffolds with arrayed holes promote cellular infiltration, neovascularization and positive host response compared to traditional 2D nanofiber membranes.

In accordance with the instant invention, nanofiber structures (sometimes referred to as scaffolds or nanofibrous herein) are provided. The nanofibers of the instant invention can be fabricated by any method. In a particular embodiment, the nanofiber structures comprise electrospun nanofibers. In a particular embodiment, the nanofiber structure comprises uniaxially aligned fibers, random fibers, and/or entangled fibers. While the application generally describes nanofibers (fibers having a diameter less than about 1 μm (e.g., average diameter)) structures and the synthesis of three-dimensional nanofibrous structures, the instant invention also encompasses microfibers (fibers having a diameter greater than about 1 μm (e.g., average diameter)) structures and the synthesis of three-dimensional microfibrous structures. In a particular embodiment, the nanofibrous structures are expanded using a subcritical fluid or liquid, particularly subcritical $CO_2$. Examples of subcritical fluids or liquids include, without limitation, $CO_2$, $N_2$, $N_2O$, hydrocarbons, and fluorocarbons. For example, nanofiber structures (e.g., mats) may be expanded by exposing to, contacting with or being placed into (e.g., submerged or immersed) a subcritical liquid/fluid (e.g., subcritical $CO_2$) and then depressurized. The cycle of placing the nanofibrous structures into subcritical $CO_2$ and depressurizing may be performed one or more time, e.g., at least two or three times. The nanofiber structure may be crosslinked (e.g., prior to expansion).

It is envisioned that the nanofiber scaffolds of the present invention can be formed and manufactured into a variety of shapes (e.g., round, square, rectangular), sizes, and thicknesses. For example, the nanofiber structure may be cut or shaped prior to expansion. In one embodiment, the expanded nanofiber scaffold is from about 1 to about 20 mm thick. In another embodiment, the expanded nanofiber scaffold is from about 1 to about 10 mm thick. In another embodiment, the expanded nanofiber scaffold is from about 1 to about 5 mm thick.

The nanofibers of the instant invention may comprise any polymer. In a particular embodiment, the polymer is biocompatible. The polymer may be biodegradable or non-biodegradable. In a particular embodiment, the polymer is a biodegradable polymer. The polymer may by hydrophobic, hydrophilic, or amphiphilic. In a particular embodiment, the polymer is hydrophobic. In a particular embodiment, the polymer is hydrophilic. The polymer may be, for example, a homopolymer, random copolymer, blended polymer, copolymer, or a block copolymer. Block copolymers are most simply defined as conjugates of at least two different polymer segments or blocks. The polymer may be, for example, linear, star-like, graft, branched, dendrimer based, or hyperbranched (e.g., at least two points of branching). The polymer of the invention may have from about 2 to about 10,000, about 2 to about 1000, about 2 to about 500, about 2 to about 250, or about 2 to about 100 repeating units or monomers. The polymers of the instant invention may comprise capping termini.

Examples of hydrophobic polymers include, without limitation: poly(hydroxyethyl methacrylate), poly(N-isopropyl acrylamide), poly(lactic acid) (PLA (or PDLA)), poly(lactide-co-glycolide) (PLG), poly(lactic-co-glycolic acid) (PLGA), polyglycolide or polyglycolic acid (PGA), polycaprolactone (PCL), poly(aspartic acid), polyoxazolines (e.g., butyl, propyl, pentyl, nonyl, or phenyl poly(-oxazolines)), polyoxypropylene, poly(glutamic acid), poly(propylene fumarate) (PPF), poly(trimethylene carbonate), polycyanoacrylate, polyurethane, polyorthoesters (POE), polyanhydride, polyester, poly(propylene oxide), poly(caprolactonefumarate), poly(1,2-butylene oxide), poly(n-butylene oxide), poly(ethyleneimine), poly(tetrahydrofurane), ethyl cellulose, polydipyrolle/dicabazole, starch, polyvinylidene fluoride (PVDF), polytetrafluoroethylene (PTFE), polydioxanone (PDO), polyether poly(urethane urea) (PEUU), cellulose acetate, polypropylene (PP), polyethylene terephthalate (PET), nylon (e.g., nylon 6), polycaprolactam, PLA/PCL, poly(3-hydroxybutyrate-co-3-hydroxyvalerate) (PHBV), PCL/calcium carbonate, and/or poly(styrene).

Examples of hydrophilic polymers include, without limitation: polyvinylpyrrolidone (PVP), poly(ethylene glycol) and poly(ethylene oxide) (PEO), chitosan, collagen, chondroitin sulfate, sodium alginate, gelatin, elastin, hyaluronic acid, silk fibroin, sodium alginate/PEO, silk/PEO, silk fibroin/chitosan, hyaluronic acid/gelatin, collagen/chitosan, chondroitin sulfate/collagen, and chitosan/PEO.

Amphiphilic copolymers or polymer composites may comprise a hydrophilic polymer (e.g., segment) and a hydrophobic polymer (e.g., segment) from those listed above (e.g., gelatin/polyvinyl alcohol (PVA), PCL/collagen, chitosan/PVA, gelatin/elastin/PLGA, PDO/elastin, PHBV/collagen, PLA/hyaluronic acid, PLGA/hyaluronic acid, PCL/hyaluronic acid, PCL/collagen/hyaluronic acid, gelatin/siloxane, PLLA/MWNTs/hyaluronic acid).

Examples of polymers particularly useful for electrospinning are provided in Xie et al. (Macromol. Rapid Commun. (2008) 29:1775-1792; incorporated by reference herein; see e.g., Table 1). Examples of compounds or polymers for use in the fibers of the instant invention, particularly for electrospun nanofibers include, without limitation: natural polymers (e.g., chitosan, gelatin, collagen type I, II, and/or III, elastin, hyaluronic acid, cellulose, silk fibroin, phospholipids (Lecithin), fibrinogen, hemoglobin, fibrous calf thymus Na-DNA, virus M13 viruses), synthetic polymers (e.g., PLGA, PLA, PCL, PHBV, PDO, PGA, PLCL, PLLA-DLA, PEUU, cellulose acetate, PEG-b-PLA, EVOH, PVA, PEO, PVP), blended (e.g., PLA/PCL, gelatin/PVA, PCL/gelatin, PCL/collagen, sodium aliginate/PEO, chitosan/PEO, Chitosan/PVA, gelatin/elastin/PLGA, silk/PEO, silk fibroin/chitosan, PDO/elastin, PHBV/collagen, hyaluronic acid/gelatin, collagen/chondroitin sulfate, collagen/chitosan), and composites (e.g., PDLA/HA, PCL/CaCO$_3$, PCL/HA, PLLA/HA, gelatin/HA, PCL/collagen/HA, collagen/HA, gelatin/siloxane, PLLA/MWNTs/HA, PLGA/HA). In a particular embodiment, the nanofiber comprises polymethacrylate, poly vinyl phenol, polyvinylchloride, cellulose, polyvinyl alcohol, polyacrylamide, PLGA, collagen, polycaprolactone, polyurethanes, polyvinyl fluoride, polyamide, silk, nylon, polybennzimidazole, polycarbonate, polyacrylonitrile, polyvinyl alcohol, polylactic acid, polyethylene-co-vinyl acetate, polyethylene oxide, polyaniline, polystyrene, polyvinylcarbazole, polyethylene terephthalate, polyacrylic acid-polypyrene methanol, poly(2-hydroxyethyl methacrylate), polyether imide, polyethylene glycol, poly(ethylene-co-vinyl alcohol), polyacrylnitrile, polyvinyl pyrrolidone, polymetha-phenylene isophthalamide, gelatin, chitosan, starch, pectin, cellulose, methylcellulose, sodium polyacrylate, starch-acrylonitrile co-polymers, and/or combinations of two or more polymers. In a particular embodiment, the polymer comprises polycaprolactone (PCL). In a particular embodiment, the polymer comprises polycaprolactone (PCL) and gelatin (e.g., at a 1:1 ratio).

In a particular embodiment, the nanofiber structures comprise a material that enhances the nanofiber structure's ability to absorb fluids, particularly aqueous solutions (e.g., blood). In a particular embodiment, the nanofibers comprise a polymer and the material which enhances the absorption properties. In a particular embodiment, the nanofiber structures are coated with the material which enhances the absorption properties. The term "coat" refers to a layer of a substance/material on the surface of a structure. Coatings may, but need not, also impregnate the nanofiber structure. Further, while a coating may cover 100% of the nanofiber structure, a coating may also cover less than 100% of the surface of the nanofiber structure (e.g., at least about 75%, at least about 80%, at least about 85%, at least about 90%, at least about 95%, at least about 98%, or more the surface may be coated). Materials which enhance the absorption properties of the expanded nanofiber structures include, without limitation: gelatin, alginate, chitosan, collagen, starch, pectin, cellulose, methylcellulose, sodium polyacrylate, starch-acrylonitrile co-polymers, other natural or synthetic hydrogels, and derivatives thereof (e.g., del Valle et al., Gels (2017) 3:27). In a particular embodiment, the material is a hydrogel (e.g., a polymer matrix able to retain water, particularly large amounts of water, in a swollen state). In a particular embodiment, the material is gelatin. In a particular embodiment, the expanded nanofiber structures are coated with about 0.05% to about 10% coating material (e.g., gelatin), particularly about 0.1% to about 10% coating material (e.g., gelatin) or about 0.1% to about 1% coating material (e.g., gelatin). In a particular embodiment, the material (e.g., hydrogel) is crosslinked.

In a particular embodiment, the nanofiber structures of the instant invention are crosslinked. For example, the nanofiber structures of the instant invention may be crosslinked with a crosslinker such as, without limitation: formaldehyde, paraformaldehyde, acetaldehyde, glutaraldehyde, a photo-crosslinker, genipin, and natural phenolic compounds (Mazaki, et al., Sci. Rep. (2014) 4:4457; Bigi, et al., Biomaterials (2002) 23:4827-4832; Zhang, et al., Biomacromolecules (2010) 11:1125-1132; incorporated herein by reference). The crosslinker may be a bifunctional, trifunctional, or multifunctional crosslinking reagent. In a particular embodiment, the crosslinker is glutaraldehyde.

As stated hereinabove, the nanofiber structures of the instant invention are expanded. Electrospun nanofibers are usually deposited on a substrate to form a nanofiber mat. However, the nanofiber mats are often dense and tightly packed. These nanofiber mats can be expanded by using a subcritical fluid, particularly subcritical $CO_2$. While the instant invention is generally described using subcritical $CO_2$, other subcritical fluids may be used as described. In a particular embodiment, the nanofibrous structure may be exposed to, contacted with, or placed into subcritical $CO_2$ and then depressurized. The nanofibrous structure may be contacted or placed into subcritical $CO_2$ and then depressurized more than once. Generally, the more times the expansion method is used the thickness and porosity of the nanofibrous (or microfibrous) structure increases. For examples, the cycle of exposure to subcritical $CO_2$ and then depressurization may be performed one, two, three, four, five, six, seven, eight, nine, ten, or more times, particularly 1-10 times, 1-5 times, or 1-3 times. In a particular embodiment, the cycle of exposure to subcritical $CO_2$ and then depressurization is performed at least 2 times (e.g., 2-5 times, 2-4 times, or 2-3 times). In a particular embodiment, the method comprises placing the nanofibrous structure and dry ice (solid $CO_2$) in a sealed container, allowing the dry ice to turn into liquid $CO_2$, and then unsealing the container to allow depressurization.

The nanofibrous structure and subcritical fluid (e.g., subcritical $CO_2$; or solid form of subcritical fluid (e.g., dry ice)) may be contained in any suitable container (e.g., one which can withstand high pressures). For example, the subcritical fluids and the nanofiber structure may be contained within, but not limited to: chambers, vessels, reactors, chambers, and tubes. In a particular embodiment, the equipment or container used during the methods of the present invention will have a feature or component that allows control of the depressurization rate of the subcritical fluid. Depressurization of the subcritical fluid can be done using a variety of methods including but not limited to manually opening the container to decrease pressure or by using some type of equipment that can regulate the rate of depressurization of the reaction vessel.

The nanofiber structure may also be expanded within a mold (e.g., made of a metal, plastic, or other material that has a defined shape and/or can withstand the subcritical fluid (e.g., subcritical $CO_2$) and depressurization) such that the expanded nanofiber structure forms a desired shape (e.g., pads, tubes, cylinders, rectangular boxes, beads, etc.). In a particular embodiment, the mold is synthesized by a 3D printer. The mold may contain holes that allow for punching corresponding holes in the nanofiber structure. The nanofiber structures of the instant invention may also be manipulated after expansion to form a desired shape (e.g., pads, tubes, beads, etc.).

As stated hereinabove, the nanofiber structures of the instant invention may also comprise holes or wells. The wells/holes may be made in the nanofiber scaffold before or after expansion of the nanofiber scaffold. In a particular embodiment, the holes of the nanofiber structures are inserted prior to expansion. In a particular embodiment, the nanofiber structure is frozen (e.g., in liquid nitrogen) prior to insertion or punching of the holes. The holes of the nanofiber structure may be any shape (e.g., square, circle). The holes of the nanofiber structure can be any size. In a particular embodiment, the holes/wells have a length/dimension or diameter of about 0.1 to about 5 mm, particularly about 0.5 to about 3 mm or about 1.0 mm. The holes may be organized within the nanofiber structure in an array (e.g., a square array). In a particular embodiment, the holes of the nanofiber structure are generally equidistant from each other. The holes/wells of the nanofiber structures may all be the same size or may be various sizes. Any number of wells may be made in the nanofiber scaffolds. In one embodiment, the number of wells is between about 1 and about 200. The wells may be made using a variety of methods. In one embodiment, a mold with preset holes is used as a template to punch wells/holes into the nanofiber scaffold. The template may be made using a variety of techniques including but not limited to 3D printing.

After expansion, the nanofiber structure may be washed or rinsed in water and/or a desired carrier or buffer (e.g., a pharmaceutically or biologically acceptable carrier). Trapped gas bubbles may be removed by applying a vacuum to the nanofiber structure. For example, the expanded nanofiber structure may be submerged or immersed in a liquid (e.g., water and/or a desired carrier or buffer) and a vacuum may be applied to rapidly remove the gas bubbles. After expansion (e.g., after rinsing and removal of trapped gas), the nanofiber structures may be stored in a cold solution, lyophilized and/or freeze-dried.

The nanofiber structures of the instant invention may also be sterilized. For example, the nanofiber structures can be sterilized using various methods (e.g., by treating with ethylene oxide gas, gamma irradiation, or 70% ethanol).

The holes/wells of the nanofiber structure of the instant invention may comprise cells or tissue. In a particular embodiment, the cells are autologous to the subject to be treated with the nanofiber structure. Any cell type can be added to the holes/wells. In a particular embodiment, the cells comprise stem cells. In a particular embodiment, the cells comprise dermal fibroblasts. In a particular embodiment, the holes/wells contain cell spheroids. In a particular embodiment, the holes/wells comprise tissue samples (e.g., minced tissue), such as skin tissue samples or bone samples. In a particular embodiment, the tissue samples have a length/dimension of diameter of about 0.1 to about 5 mm, particularly about 0.5 to about 3 mm or about 1.0 mm. The cells or tissue may be cultured with in the holes/wells of the nanofiber structure (e.g., the cells or tissue may be cultured for sufficient time to allow for infiltration into the nanofiber structure). For example, the cells or tissue may be cultured in the nanofiber structure for 1 day, 2 days, 3 days, 4 days, 5 days, or more.

The nanofiber structures of the instant invention may comprise or encapsulate at least one agent, particularly a bioactive agent such as a drug or therapeutic agent (e.g., analgesic, growth factor, anti-inflammatory, signaling molecule, cytokine, antimicrobial (e.g., antibacterial, antibiotic, antiviral, and/or antifungal), blood clotting agent, factor, or protein, etc.). In a particular embodiment, the agent is hydrophilic. The agent may be added to the nanofiber structures during synthesis and/or after synthesis. The agent may be conjugated to the nanofiber structure and/or coating material, encapsulated by the nanofiber structure, and/or coated on the nanofiber structure (e.g., with, underneath, and/or on top of the coating that enhances the nanofiber structure's ability to absorb fluids). In a particular embodiment, the agent is not directly conjugated to the nanofiber structure (e.g., encapsulated). In a particular embodiment, the agent is conjugated or linked to the nanofiber structure (e.g., surface conjugation or coating). In a particular embodiment, the agents are administered with but not incorporated into the expanded nanofiber structures.

In a particular embodiment, the agents enhance tissue regeneration, tissue growth, and wound healing (e.g., growth factors). In a particular embodiment, the agent treats/prevents infections (e.g., antimicrobials such as antibacterials, antivirals and/or antifungals). In a particular embodiment, the agent is an antimicrobial, particularly an antibacterial. In a particular embodiment, the agent enhances wound healing and/or enhances tissue regeneration (e.g., bone, tendon, cartilage, skin, nerve, and/or blood vessel). Such agents include, for example, growth factors, cytokines, chemokines, immunomodulating compounds, and small molecules. Growth factors include, without limitation: platelet derived growth factor (PDGF), vascular endothelial growth factor (VEGF), epidermal growth factor (EGF), fibroblast growth factor (FGF, multiple isotypes; e.g. basic fibroblast growth factor (bFGF)), insulin-like growth factor (IGF-1 and/or IGF-2), bone morphogenetic protein (e.g., BMP-2, BMP-7, BMP-12, BMP-9), transforming growth factor (e.g., TGFβ, TGFβ3), nerve growth factor (NGF), neurotrophic factor, stromal derived factor-1 (SDF-1), glial cell-derived neurotrophic factor (GDNF), and/or keratinocyte growth factor (KGF). Small molecules include, without limitation, simvastatin, kartogenin, retinoic acid, paclitaxel, vitamin D3, etc.

In accordance with another aspect of the instant invention, methods of synthesizing the nanofiber structures are provided. In a particular embodiment, the method comprises expanding a nanofiber structure or mat by contacting (e.g., submerging or immersing) the nanofiber structure or mat with subcritical $CO_2$ (e.g., in a sealed container) and the depressurizing. The contacting with subcritical $CO_2$ and depressurization may be repeated more than once. In a particular embodiment, the method further comprises electrospinning the nanofiber structure or mat prior to expansion. In a particular embodiment, the method comprises crosslinking the nanofiber structure or mat (e.g., before or after expansion). In a particular embodiment, the method further comprises freezing (e.g., with liquid nitrogen) the nanofiber structure or mat (e.g., before or after expansion). In a particular embodiment, the method further comprises inserting or punching holes into the nanofiber structure (e.g., before or after expansion). In a particular embodiment, the method further comprises washing and/or sterilizing the expanded nanofiber structure. In a particular embodiment, the method further comprises seeding cells and/or tissue into the holes or wells of the expanded nanofiber structure. In a particular embodiment, the method further comprises plasma treatment of the nanofiber mat or structure prior to expansion. In a particular embodiment, the holes are punched into the nanofiber structure after gas expansion. In a particular embodiment, the method further comprises culturing the cells within the nanofiber structure (e.g., allowing the cells to infiltrate the nanofiber structure from the holes/wells).

The nanofiber structures of the instant invention can be used to create complex tissue architectures for a variety of application including, without limitation: wound healing, tissue engineering, tissue growth, tissue repair, tissue regeneration, and engineering 3D in vitro tissue models. The nanofiber structures can also be combined with a variety of hydrogels or biological matrices/cues to form 3D hybrid scaffolds that can release biologically functional molecules. The tissue constructs can be used for regeneration of many tissue defects (e.g., skin, bone) and healing of various wounds (e.g., injuries, diabetic wounds, venous ulcer, pressure ulcer, burns). The nanofiber structures may be used ex vivo to generate tissue or tissue constructs/models. The nanofiber structures may also be used in vivo in patients (e.g., human or animal) for the treatment of various diseases, disorders, and wounds. In a particular embodiment, the nanofiber structure stimulates the growth of existing tissue and/or repair of a wound or defect when applied in vivo. The nanofiber scaffolds can be used for engineering, growing, and/or regeneration of a variety of tissues including but not limited to skin, bone, cartilage, muscle, nervous tissue, and organs (or portions thereof).

In accordance with the instant invention, the nanofiber structures may be used in inducing and/or improving/enhancing wound healing and inducing and/or improving/enhancing tissue regeneration. The nanofiber structures of the present invention can be used for the treatment, inhibition, and/or prevention of any injury or wound. For example, the nanofiber structures can be used to induce, improve, or enhance wound healing associated with surgery (including non-elective (e.g., emergency) surgical procedures or elective surgical procedures). Elective surgical procedures include, without limitation: liver resection, partial nephrectomy, cholecystectomy, vascular suture line reinforcement and neurosurgical procedures. Non-elective surgical procedures include, without limitation: severe epistaxis, splenic injury, liver fracture, cavitary wounds, minor cuts, punctures, gunshot wounds, and shrapnel wounds. The nanofiber structures of the present invention can also be incorporated into delivery devices (e.g., a syringe) that allow for their injection/delivery directly into a desired location (e.g., a wound such as a gunshot wound). The nanofiber structures also may be delivered directly into a cavity (such as the peritoneal cavity) using a pressurized cannula.

In accordance with the instant invention, methods for inducing and/or improving/enhancing wound healing in a subject are also provided. Methods of inducing and/or improving/enhancing tissue regeneration (e.g., blood vessel growth, neural tissue regeneration, and bone regeneration) in a subject are also encompassed by the instant invention. The methods of the instant invention comprise administering or applying a nanofiber structure of the instant invention to the subject (e.g., at or in a wound). In a particular embodiment, the method comprises administering a nanofiber structure comprising an agent as described hereinabove. In a particular embodiment, the method comprises administering a nanofiber structure to the subject and an agent as described hereinabove (i.e., the agent is not contained within the nanofiber structure). When administered separately, the nanofiber structure may be administered simultaneously and/or sequentially with the agent. The methods may comprise the administration of one or more nanofiber structures. When more than one nanofiber structure is administered, the nanofiber structures may be administered simultaneously and/or sequentially.

Definitions

The singular forms "a," "an," and "the" include plural referents unless the context clearly dictates otherwise.

As used herein, the term "electrospinning" refers to the production of fibers (i.e., electrospun fibers), particularly micro- or nano-sized fibers, from a solution or melt using interactions between fluid dynamics and charged surfaces (e.g., by streaming a solution or melt through an orifice in response to an electric field). Forms of electrospun nanofibers include, without limitation, branched nanofibers, tubes, ribbons and split nanofibers, nanofiber yarns, surface-coated nanofibers (e.g., with carbon, metals, etc.), nanofibers produced in a vacuum, and the like. The production of electrospun fibers is described, for example, in Gibson et al. (1999) AIChE J., 45:190-195.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., TrisHCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients (3rd Ed.), American Pharmaceutical Association, Washington.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

"Hydrophobic" designates a preference for apolar environments (e.g., a hydrophobic substance or moiety is more readily dissolved in or wetted by non-polar solvents, such as hydrocarbons, than by water). In a particular embodiment, hydrophobic polymers may have aqueous solubility less than about 1% wt. at 37° C. In a particular embodiment, polymers that at 1% solution in bi-distilled water have a cloud point below about 37° C., particularly below about 34° C., may be considered hydrophobic.

As used herein, the term "hydrophilic" means the ability to dissolve in water. In a particular embodiment, polymers that at 1% solution in bi-distilled water have a cloud point above about 37° C., particularly above about 40° C., may be considered hydrophilic.

As used herein, the term "amphiphilic" means the ability to dissolve in both water and lipids/apolar environments. Typically, an amphiphilic compound comprises a hydrophilic portion and a hydrophobic portion.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "antibiotic" refers to antibacterial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

As used herein, an "anti-inflammatory agent" refers to compounds for the treatment or inhibition of inflammation. Anti-inflammatory agents include, without limitation, non-steroidal anti-inflammatory drugs (NSAIDs; e.g., aspirin, ibuprofen, naproxen, methyl salicylate, diflunisal, indomethacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroids (e.g., prednisone, betamethasone, budesonide, cortisone, dexamethasone, hydrocortisone, methylprednisolone, prednisolone, tramcinolone, and fluticasone), rapamycin, acetaminophen, glucocorticoids, steroids, beta-agonists, anticholinergic agents, methyl xanthines, gold injections (e.g., sodium aurothiomalate), sulphasalazine, and dapsone.

As used herein, the term "subject" refers to an animal, particularly a mammal, particularly a human.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "analgesic" refers to an agent that lessens, alleviates, reduces, relieves, or extinguishes pain in an area of a subject's body (i.e., an analgesic has the ability to reduce or eliminate pain and/or the perception of pain).

As used herein, the term "small molecule" refers to a substance or compound that has a relatively low molecular weight (e.g., less than 2,000). Typically, small molecules are organic, but are not proteins, polypeptides, or nucleic acids.

The term "hydrogel" refers to a water-swellable, insoluble polymeric matrix (e.g., hydrophilic polymers) comprising a network of macromolecules, optionally crosslinked, that can absorb water to form a gel.

The term "crosslink" refers to a bond or chain of atoms attached between and linking two different molecules (e.g., polymer chains). The term "crosslinker" refers to a molecule capable of forming a covalent linkage between compounds. A "photocrosslinker" refers to a molecule capable of forming a covalent linkage between compounds after photoinduction (e.g., exposure to electromagnetic radiation in the visible and near-visible range). Crosslinkers are well known in the art (e.g., formaldehyde, paraformaldehyde, acetaldehyde, glutaraldehyde, etc.). The crosslinker may be a bifunctional, trifunctional, or multifunctional crosslinking reagent.

The following example is to illustrate certain embodiments of the invention. It is not intended to limit the invention in any way.

Example

Materials and Methods
Fabrication of 2D Nanofiber Membranes

PCL nanofiber mats were produced utilizing a standard electrospinning (Jiang, et al. (2015) ACS Biomater. Sci. Eng., 1:991-1001; Jiang, et al. (2016) Adv. Healthcare Mater., 5:2993-3003). Briefly, PCL (Mw=80 kDa) was dissolved in a solvent mixture consisting of dichloromethane (DCM) and N, N-dimethylformamide (DMF) with a ratio of 4:1 (v/v) at a concentration of 10% (w/v). PCL solution was pumped at a flow rate of 0.8 mL/h using a syringe pump. Coumarin 6-loaded PCL fibers were fabricated with 50 µg/mL coumarin 6 in the PCL solution. LL 37 was loaded into PCL fibers by co-axial electrospinning (Xie, J., et al. (2012) Acta Biomater., 8:811-819). The core solution was composed of 100 mg/mL pluronic F-127 and 5 mg/mL LL 37 in water. The flow rate was set at 0.08 mL/h. The sheath solution was the same PCL solution as described above. An electrical potential of 15 kV was applied between the spinneret (a 22-gauge needle) and a grounded collector located 20 cm apart from the spinneret. Aligned nanofiber mats were collected on a drum with rotating speeds of 2000 rpm. The fabricated PCL nanofiber mats and coumarin 6-loaded PCL nanofiber mats were about 1 mm thick. LL 37-loaded PCL nanofiber mats were about 100 µm thick. The raw PCL fiber mats were punched by a 0.5 mm-diameter punch in liquid nitrogen to generate arrayed holes.

Fabrication of 3D Electrospun Nanofiber Scaffolds

PCL nanofiber mats, coumarin 6-loaded PCL nanofiber mats, LL 37-loaded PCL nanofiber mats, and PCL nanofiber mats with arrayed holes were first cut into 1 cm×1 cm squares in liquid nitrogen to avoid deformation on the edges. Next, ~1 g of dry ice and one piece of nanofiber mat were put into a 30 mL Oak Ridge centrifuge tube. After the dry ice changed into $CO_2$ fluid, the cap rapidly loosened and the puffed nanofiber scaffold was removed from the tube. This expanding procedure was repeated until the desired thickness was reached. The nanofiber scaffolds were sterilized by ethylene oxide before incubation with bacteria.

Characterization of 3D Nanofiber Scaffolds

Based on the volume change of nanofiber scaffolds, the porosity was estimated using the following equation: $\varepsilon=(V-V_0)/V \times 100\%$ where $\varepsilon$ is porosity, $V=L$ (length)×W (width)×T (thickness) is the volume of PCL nanofiber scaffold, $V_0=m_0/\rho_0$ is the calculated volume of the bulk PCL material, $m_0$ is the mass of the bulk PCL material, and $\rho_0$ is the density of the bulk PCL materials (Jiang, et al. (2015) ACS Biomater. Sci. Eng., 1:991-1001). PCL nanofiber mats before and after expansion were embedded in deionized water and frozen at −20° C. Cross sections of nanofiber scaffolds were obtained by a cryostat and then freeze-dried. Scanning electron microscopy (SEM) (FEI, Quanta 200, Oregon) was used to characterize the morphologies of cross sections of nanofiber scaffolds. To avoid charging, nanofiber samples were fixed on a metallic stud with double-sided conductive tape and coated with platinum for 4 minutes in a vacuum at a current intensity of 10 mA using a sputter coater. SEM images were acquired at an accelerating voltage of 30 kV. The gap distances and layer thicknesses of nanofiber scaffolds after expanding once and twice were measured based on SEM images using the Image J software. At least 250 gaps or layers were analyzed.

Coumarin 6-Loaded 3D Nanofiber Scaffolds

For comparison, coumarin 6-loaded PCL nanofiber mats were expanded in 1 M $NaBH_4$ for 1 hour. The procedure was performed as described (Jiang, et al. (2015) ACS Biomater. Sci. Eng., 1:991-1001; Jiang, et al. (2016) Adv. Healthcare Mater., 5:2993-3003). The top surface of $CO_2$ expanded coumarin 6-loaded nanofiber scaffolds, $NaBH_4$ expanded coumarin 6-loaded nanofiber scaffolds, raw coumarin 6-loaded nanofiber mats, and raw PCL fiber mats were observed by a fluorescence microscope with an excitation wavelength at 488 nm and emission wavelength at 530±20 nm and the images were taken by a CCD camera with the same exposure time. The experiments were carried out at least three times. The fluorescent intensity was quantified using Image J software.

LL 37-Loaded 3D Nanofiber Scaffolds

In vitro release kinetics of LL 37 from nanofiber membranes before and after expansion was evaluated by immersing 5 mg fiber samples in 5 mL PBS at 37° C. The supernatants were collected at each time point and replaced with fresh PBS solutions. The LL 37 concentrations for all collected samples were determined by an LL 37 ELISA kit according to the manufacturer's instructions.

*P. aeruginosa* was used to evaluate the anti-bacteria activity of LL 37-loaded fiber membranes before and after expansion. Briefly, *P. aeruginosa* was cultured in liquid Luria-Bertani (LB) medium overnight in a shaking incubator at 37° C. at 220 rpm overnight. Then, 20 μL suspended bacteria were transferred to 4 mL fresh LB medium and incubated for an additional 2 hours at 37° C. at 220 rpm. The bacterial suspension was centrifuged at 12000 rpm for 10 minutes. The cell pellet was re-suspended in 1 mL PBS after removal of supernatant. This procedure was repeated once. The $OD_{660}$ value of bacterial suspension was determined using a NanoDrop (Thermo Scientific, Wilmington, Del.). The value of $OD_{660}$ is approximately equal to $1.0 \times 10^8$ CFU bacteria. The cells were diluted into $1.0 \times 10^5$, $1.0 \times 10^6$ and $1.0 \times 10^7$ CFU bacteria with PBS and added 5 mg PCL fibers, unexpanded LL 37-loaded PCL fibers and expanded LL 37-loaded PCL fibers to 5 mL medium containing bacteria, and then placed the culture on a shaker at 37° C. at 220 rpm for 1 hour. Then, the culture was then spread on a LB agar plate. After incubation for 12 hours at 37° C., the number of colonies was counted. The counts were repeated with three LB agar plates and averaged.

Fabrication and Subcutaneous Implantation of 3D Nanofiber Scaffolds with Arrayed Holes Electrospun nanofiber membranes were first frozen at temperatures lower than glass transition temperatures (e.g., immersed in liquid nitrogen) to make them brittle and the holes in a square array through nanofiber membranes were created by a micro-punch. After ethylene oxide gas sterilization, expanded PCL nanofiber scaffolds with arrayed holes (10 mm×10 mm×10 mm) were coated with 0.5% gelatin and cross-linked to prevent collapse, and then cut into 1 mm thick and soaked in saline, followed by subcutaneous implantation into 9-week old Sprague Dawley (SD) rats (250-300 g). Briefly, the rats were anesthetized using 4% isoflurane in oxygen for approximately 2 minutes. Rats were placed on a heating pad to maintain their body temperature. An area of 8×4 cm² on the back of each animal was shaved, and povidone-iodine solution was applied three times on the exposed skin. Each rat received 4 implants; subcutaneous pockets were made through 1.5 cm incisions at 4 supraspinal sites on the dorsum. Each implant was gently inserted into a subcutaneous pocket under the skin to avoid compressing, and then the skin incisions were closed with a stapler. Rats were euthanized by $CO_2$ at 1, 2, and 4 weeks post-implantation. Each explant with surrounding tissue was gently dissected out of its subcutaneous pocket, and then immersed in formalin for at least 3 days prior to histology analysis.

Histological and Immunohistochemical Analysis

Fixed samples were dehydrated in a graded ethanol series (70%-100%), embedded in paraffin, and then sectioned (4 μm). Samples were performed with either hematoxyline and eosin (H & E) or masson's trichrome staining. Immunohistochemical staining was performed to characterize macrophage phenotypes responding to expanded nanofiber scaffolds with arrayed holes. Slides were deparaffinized followed by antigen retrieval in heated citrate buffer for 10 minutes (10 mM citrate, pH 6.0 at 95-100° C.). Peroxidase was blocked by incubating sections in 3% $H_2O_2$ for 5 minutes. Non-specific antibody binding was prevented with blocking solution (2% normal goat serum, 0.1% triton X-100 in PBS; 1 hour at room temperature). Sections were decanted and incubated with primary antibodies diluted 1:200 in blocking solution, overnight at 4° C. Primary antibodies against the pan-macrophage marker CD68, M1 macrophage marker CCR 7 and M2 macrophage marker CD206 were used.

Histomorphometric and Macrophage Phenotype Quantification

Microscopic images of H & E staining, Masson's trichrome staining, and immunohistochemical staining of CD68, CCR7, and CD206 were all obtained with a Ventana's Coreo Au™ slide scanner, and edited with Ventana image viewer v. 3.1.3. The magnifications were set at 4×, 10×, and 40×, and then snapshots were taken at three random locations on each sample. The number of blood vessels was measured using Ventaina image viewer. The number of blood vessels was converted into counts per mm². All the foreign body giant cells in each specimen were quantified by masson's trichrome staining images. In vivo experimental data was obtained from three independent experiments. Images were captured with a Ventana's Coreo Au™ slide scanner. Three sections were evaluated for each implant. A total of 6 snapshots of CD68, CCR7 and CD163 positive immunohistochemical staining images at 40× magnification were randomly collected on each tissue section. The number of positive cells in each snapshot was quantified.

Statistical Analysis

Each data point represents the mean of three replicates. The statistical analysis was performed on the means of the data obtained from at least three independent experiments. All the results were given as means and were compared using an analysis of variance (ANOVA) followed by LSD post hoc assessment for evaluating statistical intra- and inter-individual differences, with significance set at $p<0.05$.

Results

Fabrication and Characterization of 3D Electrospun Nanofiber Scaffolds

For the fabrication methodology, electrospun PCL nanofiber mats were generated and the mats were cut into desired sizes (e.g., 1 cm×1 cm) (Jiang, et al. (2015) ACS Biomater. Sci. Eng., 1:991-1001; Jiang, et al. (2016) Adv. Healthcare Mater., 5:2993-3003). Then, the nanofiber membranes were placed in a centrifuge tube in the presence of dry ice at room temperature and the cap was tightened. After the dry ice changed into liquid, the $CO_2$ fluid was rapidly depressurized, resulting in the formation of 3D nanofiber scaffolds (FIG. 1A). Based on calculations (Redlich-Kwong equation), the $CO_2$ liquid is in a subcritical state. The thickness of 3D nanofiber scaffolds can be tailored by increasing the number of $CO_2$ fluid processing times (FIG. 1B). The thickness of nanofiber mats increased from 1 mm to 2.5 mm and further to 10 mm after the first and second treatments with subcritical $CO_2$ fluid.

The porosity of aligned PCL nanofiber scaffolds increased with increasing the number of processing times, which corresponded with the increased thickness (FIG. 1C). The porosity of the nanofiber scaffolds increased from 78.5% for the raw nanofiber mats to 92.1% and 99.0% after the first and second treatment with subcritical $CO_2$ fluid (FIG. 1D). To maintain the integrity of the nanofiber scaffolds following expansion, the scaffolds were embedded in ice from frozen water and sectioned by a microtome to expose the x-y, y-z plans and then freeze-dried using a lyophilizer. To reveal the detailed structure, the sectioned samples were examined by scanning electron microscopy (SEM). Prior to expansion, aligned electrospun PCL nanofiber mats were composed of densely packed fibrillar structures (FIGS. 1E and 1F) (Jiang, et al. (2015) ACS Biomater. Sci. Eng., 1:991-1001). In contrast, nanofiber scaffolds expanded by subcritical $CO_2$ fluid displayed layered structures with preserved nanotopographic cues rendered by aligned nanofibers (FIGS. 1G and 1H), which was critical for regeneration of tendon, muscle, and nerve tissues and akin to the nanofiber scaffolds expanded in $NaBH_4$ solutions (Jiang, et al. (2015) ACS Biomater. Sci. Eng., 1:991-1001; Jiang, et al. (2016) Adv. Healthcare Mater., 5:2993-3003). It was confirmed that 3D nanofiber scaffolds expanded by subcritical $CO_2$ fluid had a similar structure as the ones generated using a gas production chemical reaction in an aqueous solution (Jiang, et al. (2015) ACS Biomater. Sci. Eng., 1:991-1001; Jiang, et al. (2016) Adv. Healthcare Mater., 5:2993-3003). In addition, it seems that the layer thickness decreased with increasing treatment times while no significant difference was observed for the gap distance distributions for scaffolds after expanding once and twice. Further, the expansion of nanofiber membranes made of water-soluble polymers (e.g., polyvinylpyrrolidone (PVP)) was demonstrated (FIG. 2), which could not be achieved using previous methods (Jiang, et al. (2015) ACS Biomater. Sci. Eng., 1:991-1001; Jiang, et al. (2016) Adv. Healthcare Mater., 5:2993-3003; Joshi, et al. (2015) Chem. Eng. J., 275:79-88; Sheikh, et al. (2015) Nanomedicine: NBM, 11:681-691; Lee, et al. (2011) Tissue Eng. Part A, 17:2695-2702).

Figure 3A:
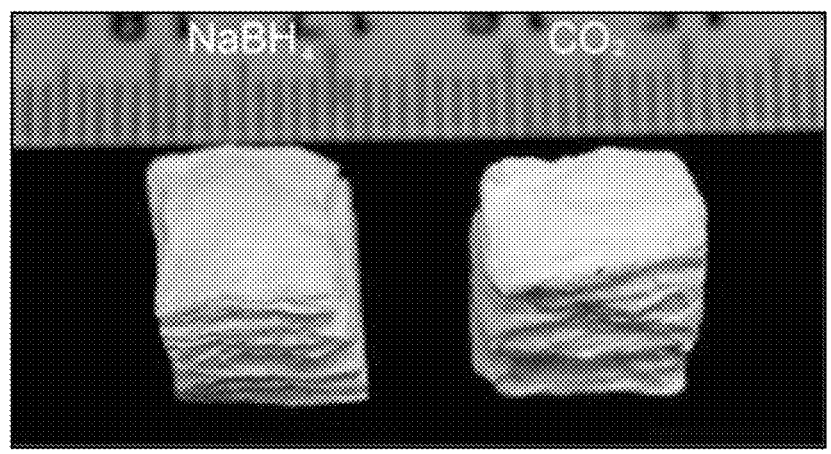
FIGS. 3A-3C shows expansion of coumarin 6-loaded PCL nanofiber scaffolds.
Figure 3B:
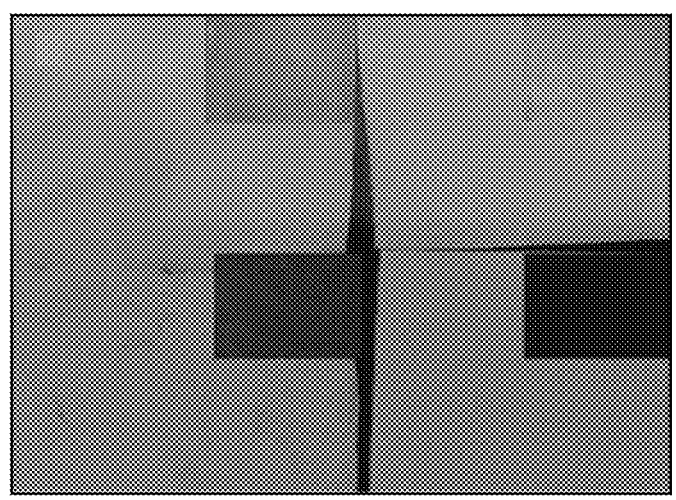
Figure 3C:
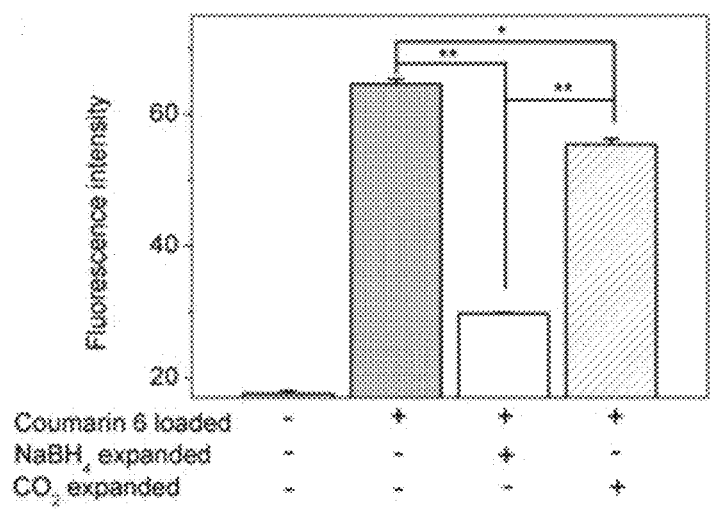

The Effect of Subcritical $CO_2$ Processing on the Encapsulated Molecules 3D scaffolds provide not only a substrate for cell attachment and growth but also a local device for delivering therapeutic agents for regulating cellular responses or host immune response after implantation. To demonstrate the advantages of the current manufacturing approach, both hydrophobic and hydrophilic molecules were encapsulated in the nanofiber scaffolds. Coumarin 6, a small hydrophobic fluorescent dye molecule, was selected as a model drug in that a number of small molecules have been examined for use in tissue regeneration (Ding, et al. (2005) Curr. Top. Med. Chem., 5:383-395; Lu, et al. (2014) Drug Discovery Today 19:801-808). Coumarin 6 was encapsulated into PCL nanofiber mats (Xie, et al. (2006) Pharm. Res., 23:1817-1826). A 1 M $NaBH_4$ solution or subcritical $CO_2$ fluid was used to expand the nanofiber mat from 2D to 3D. The green color of coumarin 6 faded after 1 M $NaBH_4$ solution treatment due to the high reducibility of $NaBH_4$ (FIG. 3). In contrast, scaffolds expanded by subcritical $CO_2$ fluid were still in green color (FIG. 3). The top views of each sample were also imaged by fluorescent microscopy (FIG. 3). Pristine PCL fiber samples showed no fluorescence at 488 nm (FIG. 3, bottom right). However, coumarin 6-loaded PCL fiber mats showed the strongest fluorescence (FIG. 3, top right). The fluorescent intensity of $NaBH_4$ solution expanded samples was much lower than subcritical $CO_2$ fluid expanded ones. Quantitative analysis of fluorescent intensity using Image J software showed that PCL nanofibers exhibited a very low fluorescent intensity (FIG. 3). The fluorescent intensity of subcritical $CO_2$ fluid expanded samples was significantly higher than that of $NaBH_4$ solution expanded samples. The slightly disparity in the fluorescent intensity between coumarin 6-loaded PCL nanofiber mats and subcritical $CO_2$ fluid expanded nanofiber mats could be due to the structural differences (e.g., different fiber densities).

Figure 4A:
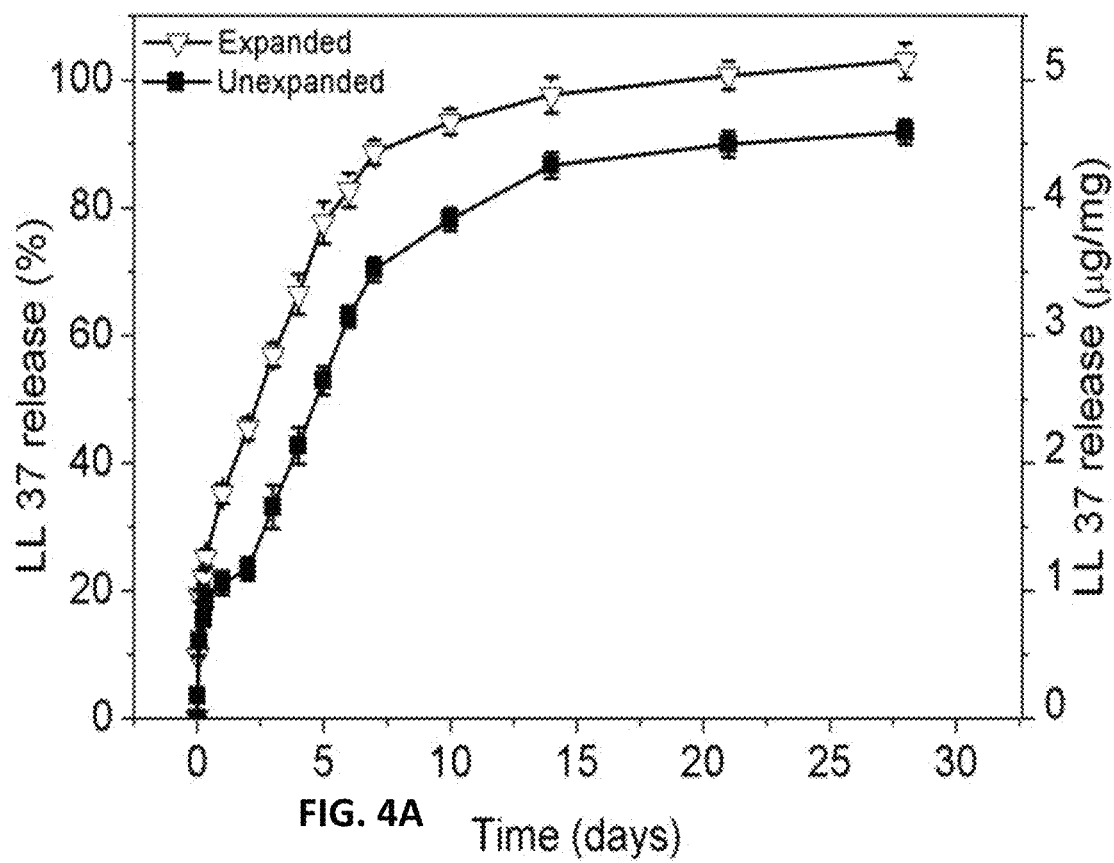
FIGS. 4A-4B show the expansion of LL37-loaded PCL nanofiber scaffolds using $CO_2$ fluid.

As for another model drug, the antimicrobial peptide called LL-37 was selected. It is a hydrophilic molecule that has been used to treat infections, promote wound healing, enhance angiogenesis, and modulate the immune response (Fumakia, et al. (2016) Mol. Pharm., 13:2318-2331; Chereddy, et al. (2014) J. Controlled Rel., 194:138-147; Durr, et al. (2006) Biochim. Biophys. Acta, 1758:1408-1425). LL37 and pluronic F127 (a surfactant) were encapsulated in the core of LL37/pluronic F127-PCL core-sheath fibers using co-axial electrospinning (Xie, et al. (2012) Acta Biomater., 8:811-819). The resulted LL37-loaded nanofiber mats were expanded using the subcritical $CO_2$ fluid. The initial drug loading was 5 μg LL 37 per 1 mg PCL nanofibers. In vitro release kinetics of LL 37 from both nanofiber mats before and after expansion in subcritical $CO_2$ fluid were determined using a LL 37 ELISA kit (FIG. 4A). About 75% and 80% LL 37 were released from raw and expanded fiber samples in the first week, respectively. The release rate of expanded fiber scaffolds was slightly higher than unexpanded samples, which may be due to the higher porosity.

Figure 4B:
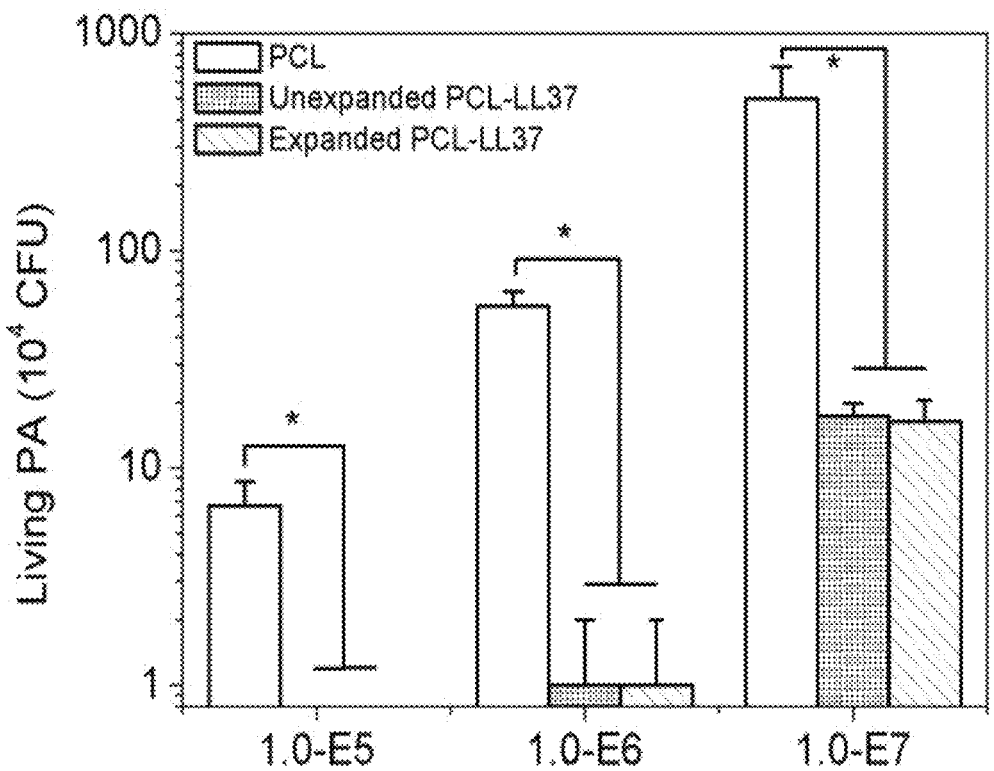

To test the retention of bioactivity of encapsulated LL-37 after expansion, the antibacterial performance of LL-37-loaded nanofiber mats was measured before and after expansion (FIG. 4B). 1 mg unexpanded LL37-loaded PCL fiber mats and expanded 3D LL37-loaded PCL fiber scaffolds were co-incubated with $1.0 \times 10^5$, $1.0 \times 10^6$, and $1.0 \times 10^7$ CFU *P. aeruginosa* bacteria in 1 ml PBS for 1 hour using pristine PCL fiber mats as a control. As expected, pristine PCL fiber mats showed no bacterial killing effect. Both expanded and unexpanded LL37-loaded PCL fiber membranes showed a similar level of bacterial killing effect (FIG. 4B), which indicates that the subcritical $CO_2$ processing had no influence on the bioactivity of encapsulated antimicrobial peptides. Therefore, it is confirmed that 3D nanofiber scaffolds expanded by subcritical $CO_2$ fluid better maintained the activity of encapsulated bioactive materials compared to previous approaches (Jiang, et al. (2015) ACS Biomater. Sci. Eng., 1:991-1001; Jiang, et al. (2016) Adv. Healthcare Mater., 5:2993-3003).

Fabrication of Expanded 3D Nanofiber Scaffolds with Arrayed Holes

Figure 4C:
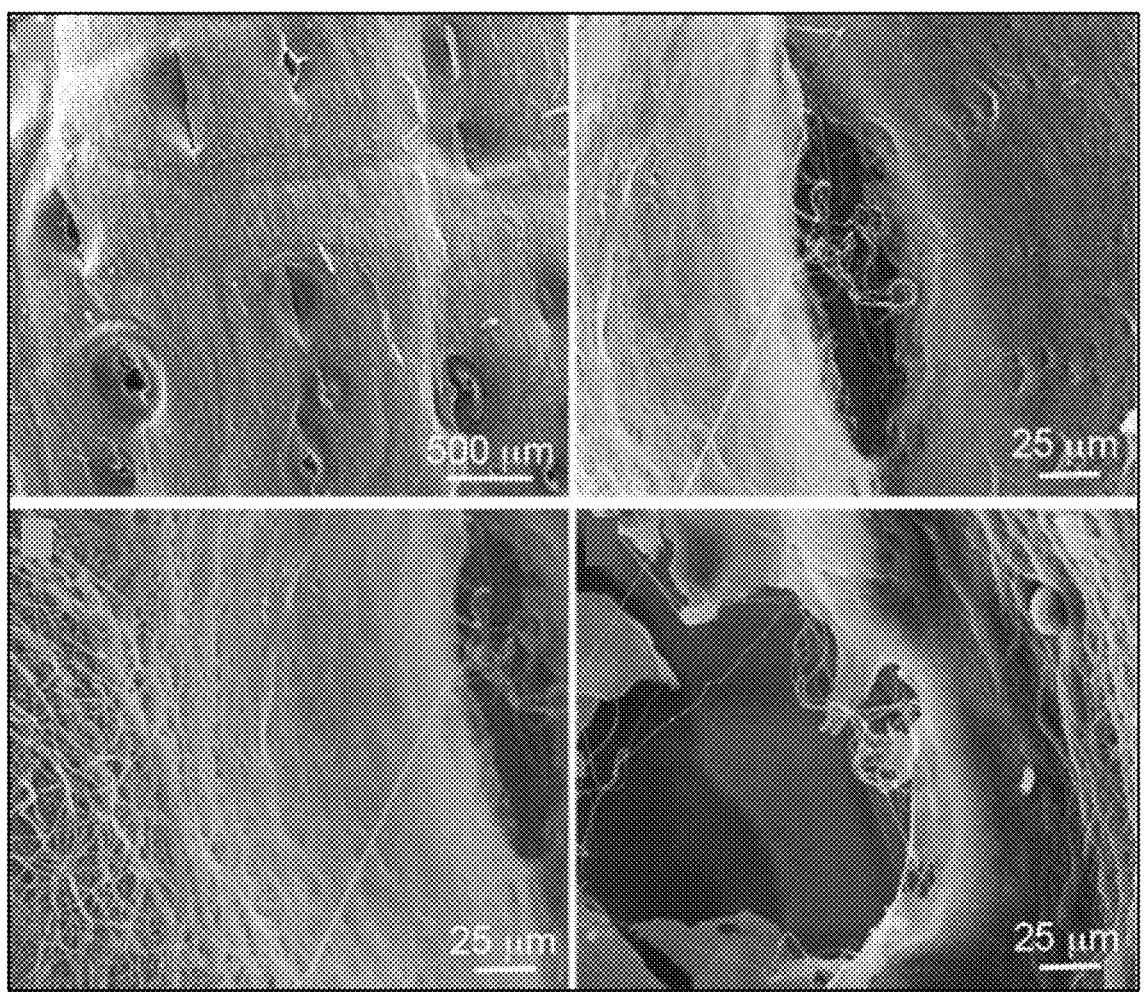
FIG. 4C provides SEM images showing nanofiber scaffolds that were punched at room temperature. Top left: Punches holes on the nanofiber scaffolds. Top right: High magnification of top left view showing the punched hole. Bottom left: High magnification of top left view showing the wall of punched holes. Bottom right: High magnification of top left view showing the bottom of punched holes. The area around the punched hole shows a lack of the nanofibrous morphology.
Figure 4D:
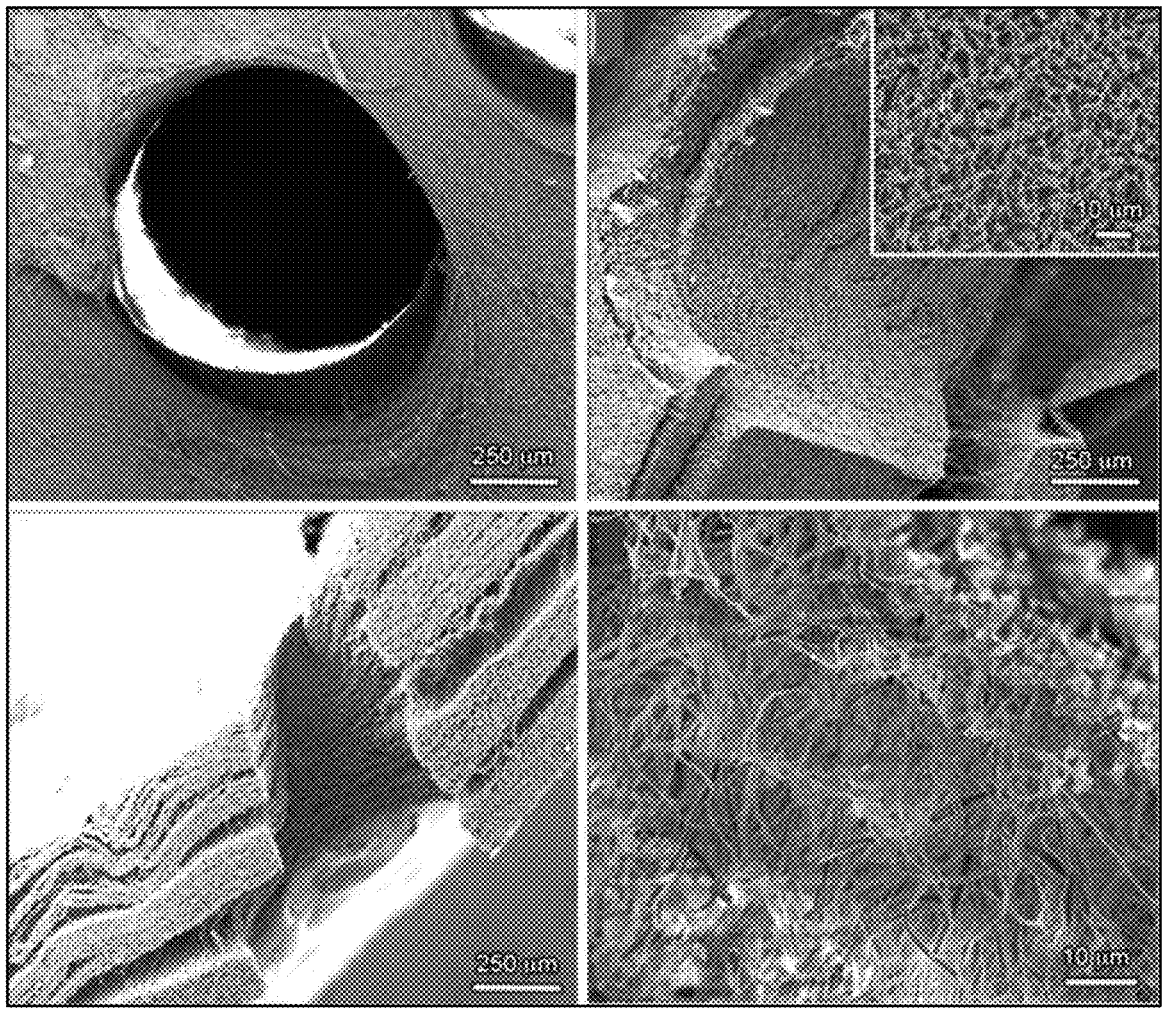
FIG. 4D shows the expansion of punched PCL nanofiber scaffolds. Top left: SEM images of punched aligned nanofiber scaffolds before expansion. Top right: SEM images showing cross-sectional morphologies of punched aligned nanofiber scaffolds before expansion. Inset: high magnification of cross-sectional area of punched aligned nanofiber scaffolds before expansion. Bottom left: SEM images showing cross-sectional morphologies of punched aligned nanofiber scaffolds after expansion. Bottom right: High magnification of cross-sectional area of punched aligned nanofiber scaffolds after expansion.

Transformation of electrospun nanofiber membranes from 2D to 3D increases the thickness and porosity of nanofiber scaffolds; however, cellular infiltration can only occur from the sides instead and not from the top and bottom surfaces of expanded scaffolds (Jiang, et al. (2016) Adv. Healthcare Mater., 5:2993-3003). Although trans-layer vascularization is not a necessity for tissue regeneration (Mahjour, et al. (2016) J. Biomed. Mater. Res. A, 104:1479-1488), cellular infiltration across different layers could benefit neotissue formation and its integration into surrounding tissues. To overcome this limitation, PCL nanofiber membranes were immersed in liquid nitrogen to make them become brittle and arrayed holes were generated through membranes using a micro-punch under cryogenic conditions. This method showed no damage or deformation to the nanofiber morphology on the surface of punched holes unlike laser sintering or room temperature punching (FIG. 4C) (Walthers, et al. (2014) Biomaterials 35:5129-5137; Bonvallet, et al. (2014) Tissue Eng. Part A, 20:2434-2445). The punched nanofiber membranes were expanded to 3D scaffolds using the subcritical $CO_2$ fluid (FIG. 4D). The layered structure was preserved and the surface of holes indicated the fiber morphology remained intact (FIG. 4D). This approach further increased the porosity of expanded 3D nanofiber scaffolds.

In Vivo Response of Expanded 3D Nanofiber Scaffolds with Arrayed Holes

Figure 5E:
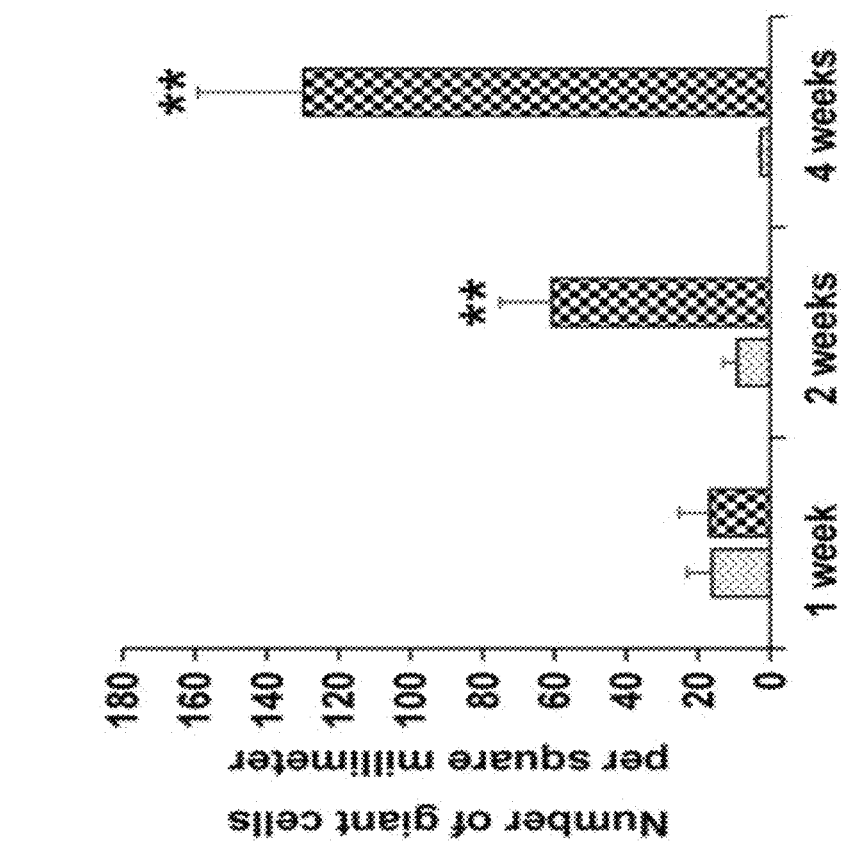
Figure 5F:
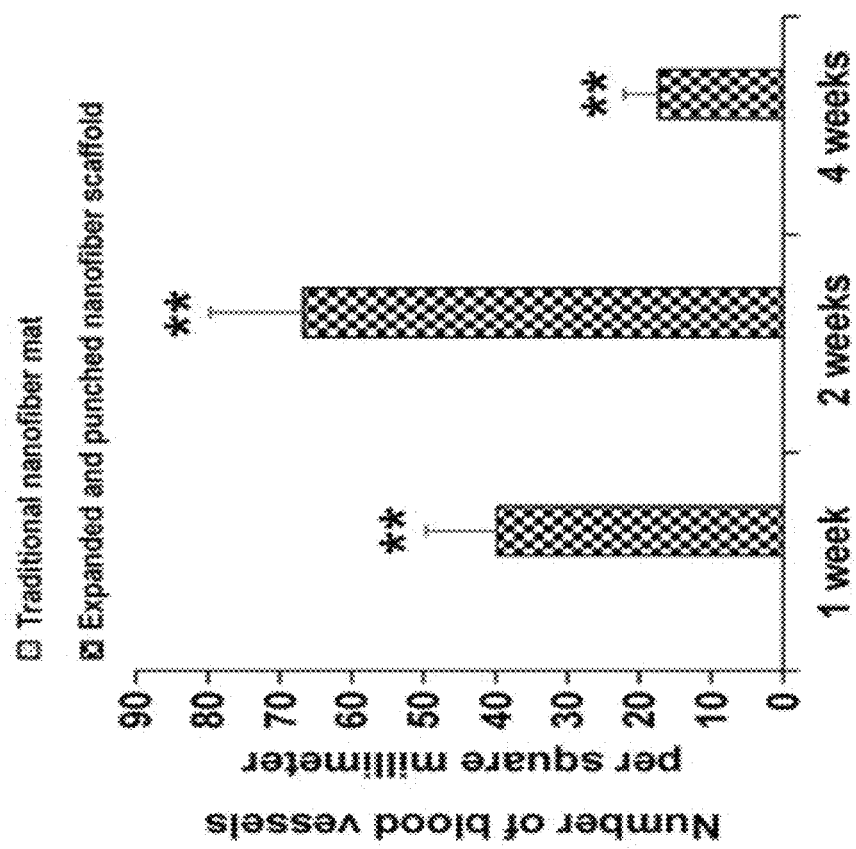
Figure 5G:
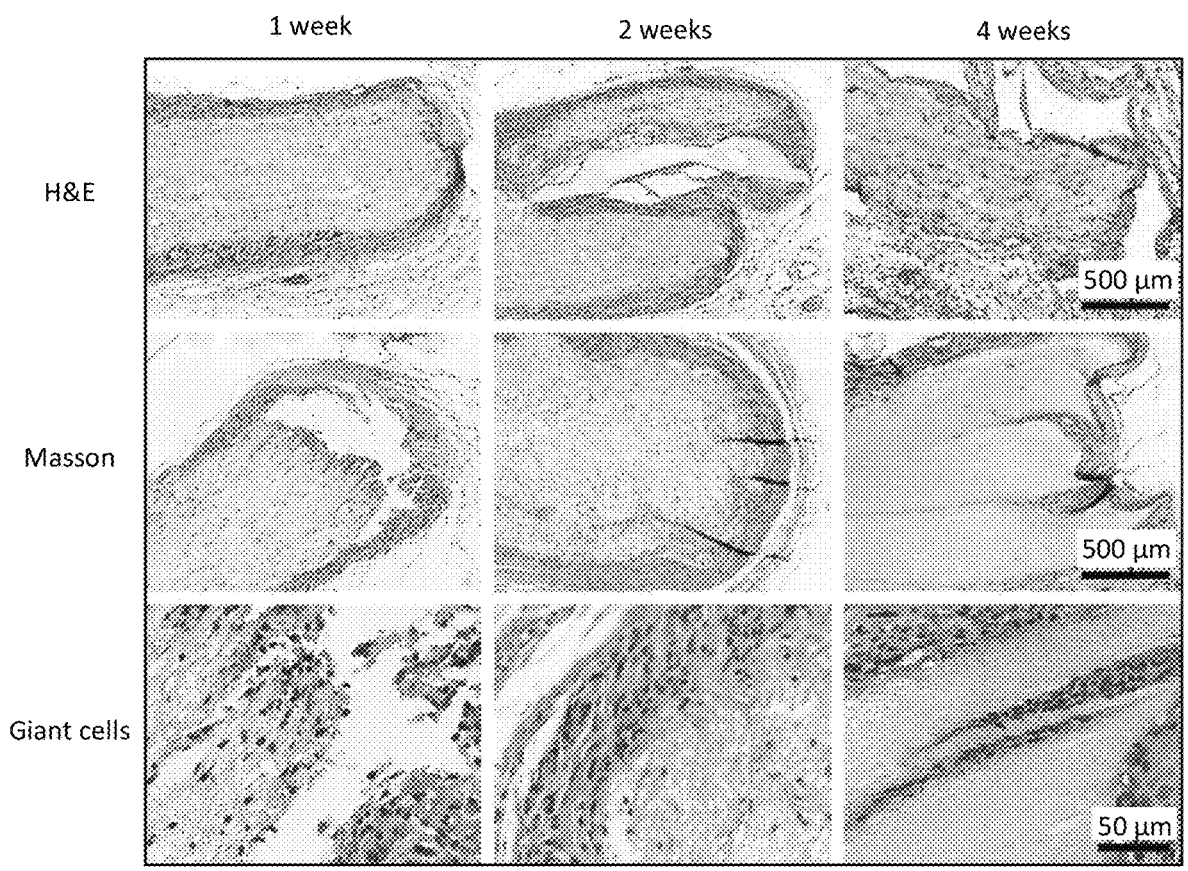
FIG. 5G provides representative H & E staining and Masson's trichrome staining images of traditional nanofiber mats and surrounding tissues after subcutaneous implantation in rats.

To further test the effect of expansion and punched holes on in vivo response, 3D expanded nanofiber scaffolds with arrayed holes were implanted subcutaneously in rats for 1 week, 2 weeks and 4 weeks, respectively. It seems that cells grew into the punched holes and then penetrated into the space between thin nanofiber layers within expanded nanofiber scaffolds (FIG. 5). Masson's trichrome staining showed the collagen deposition indicated by green arrows from infiltrated cells in the punched holes and in the gaps between thin nanofiber layers (FIG. 5B). Many blood vessels were also formed within the newly formed tissues in the holes or gaps between thin nanofiber layers (FIG. 5C). Multinucleated giant cells were also present (FIG. 5D). Numbers of blood vessels per $mm^2$ were around 39, 66, and 17 at week 1, 2 and 4, respectively (FIG. 5E). More blood vessels formed at week 2 could be attributed to the early inflammatory response. In contrast, no newly formed blood vessels were observed within traditional nanofiber mats (Jiang, et al. (2016) Adv. Healthcare Mater., 5:2993-3003). Numbers of multinucleated giant cells per implant for expanded 3D nanofiber scaffolds with arrayed holes were 16, 60, and 129 at week 1, 2 and 4, respectively (FIG. 5F). For comparison, the number of multinucleated giants cells per implant for traditional nanofiber mats was close to 16, but decreased to 9 and 6 at week 2 and 4 (Jiang, et al. (2016) Adv. Healthcare Mater., 5:2993-3003).

Figure 6A:
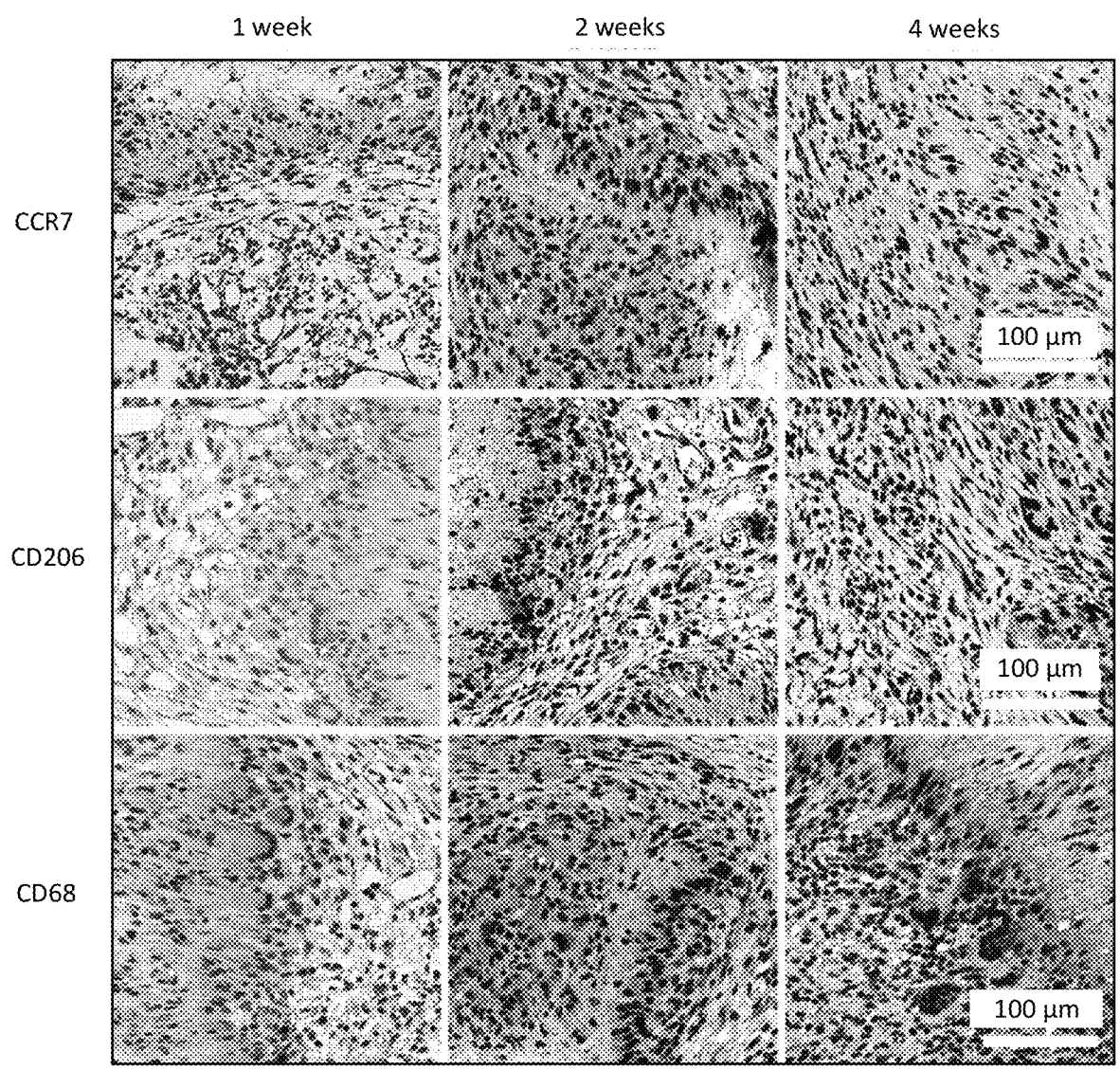
FIG. 6A provides immunohistological staining of 3D expanded nanofiber scaffolds with arrayed holes and surrounding tissues against CD68—a surface marker for pan macrophages, CD 206—a surface marker for macrophages in M2 phase, and CCR7—a surface marker for macrophages in M1 phase. The nanofiber scaffolds were subcutaneously implanted to rats for 1 week, 2 weeks, and 4 weeks.
Figure 6B:
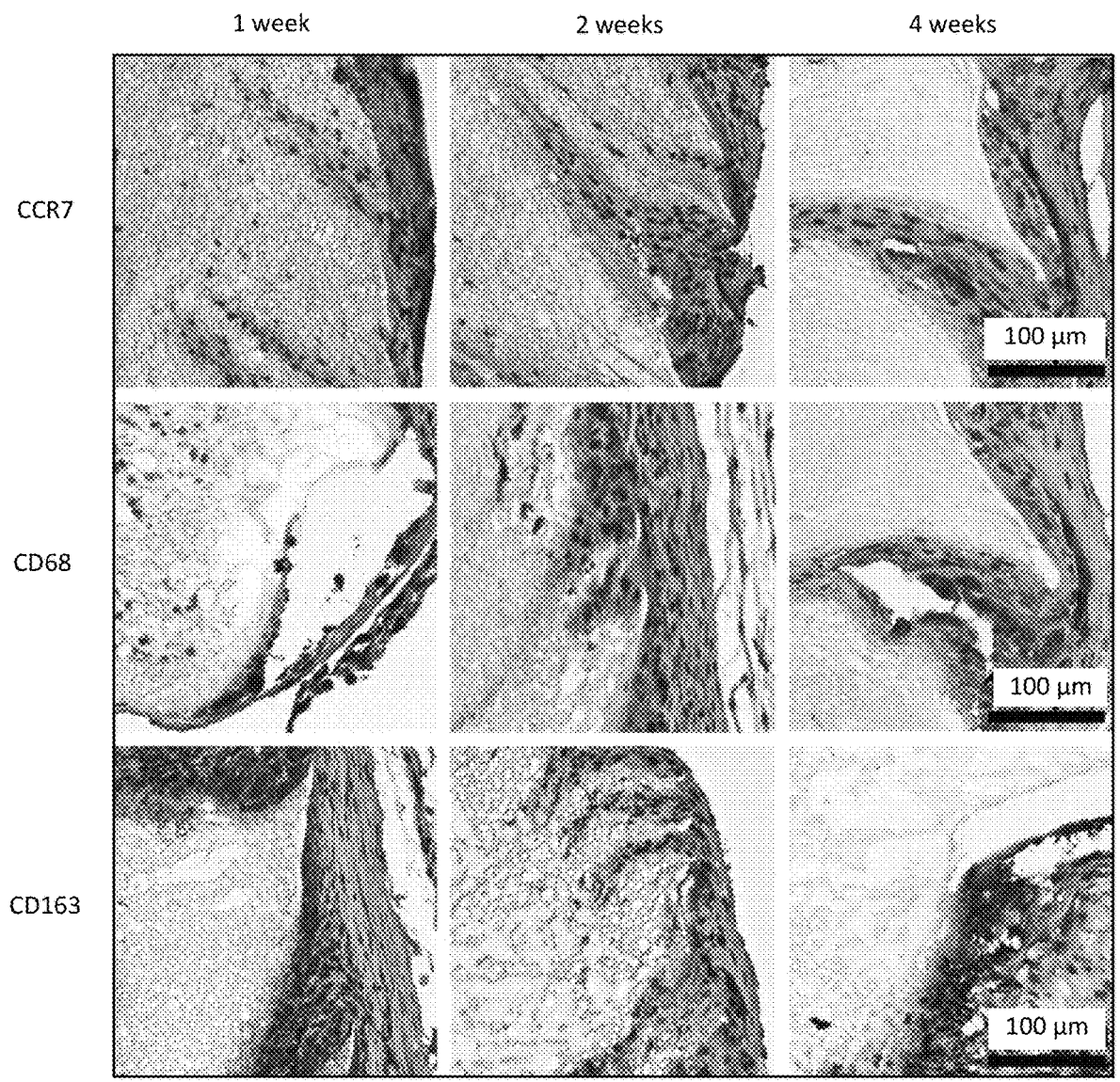
FIG. 6B provides representative immunostaining images of traditional nanofiber mats and surrounding tissues after subcutaneous implantation in rats.
Figure 7A:
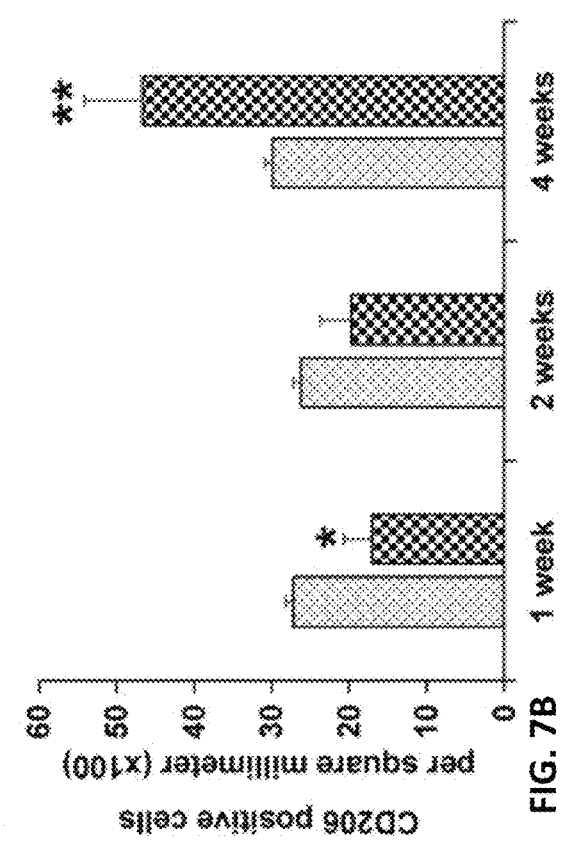
FIGS. 7A-7D shows the quantification of immunohistological analysis of 3D expanded nanofiber scaffolds with arrayed holes and traditional nanofiber mats after subcutaneous implantation. CD 68, CCR 7 (M1), CD 206 (M2) immunopositive cells and ratio of number of CD163 positive cells (M2)/number of CCR7 positive cells (M1) are shown. The values were obtained by measuring six scanning images at 40× (objective lens) magnification for each specimen.
Figure 7C:
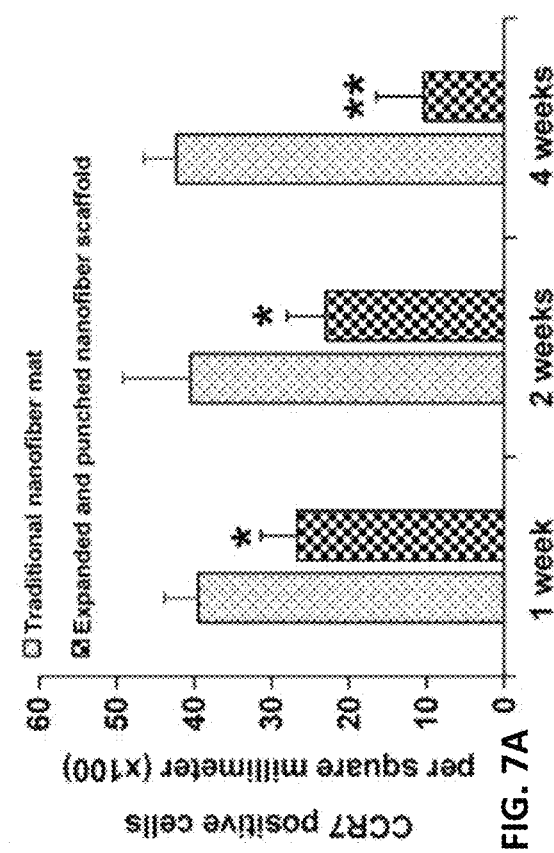
Figure 7B:
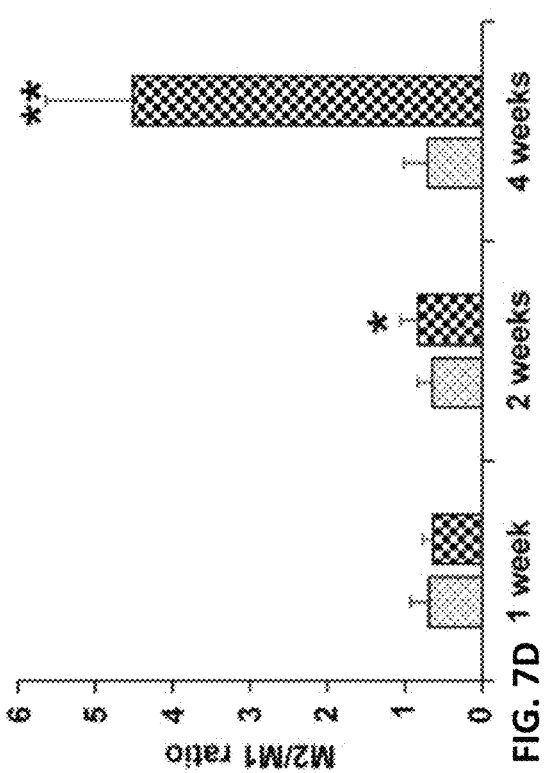
Figure 7D:
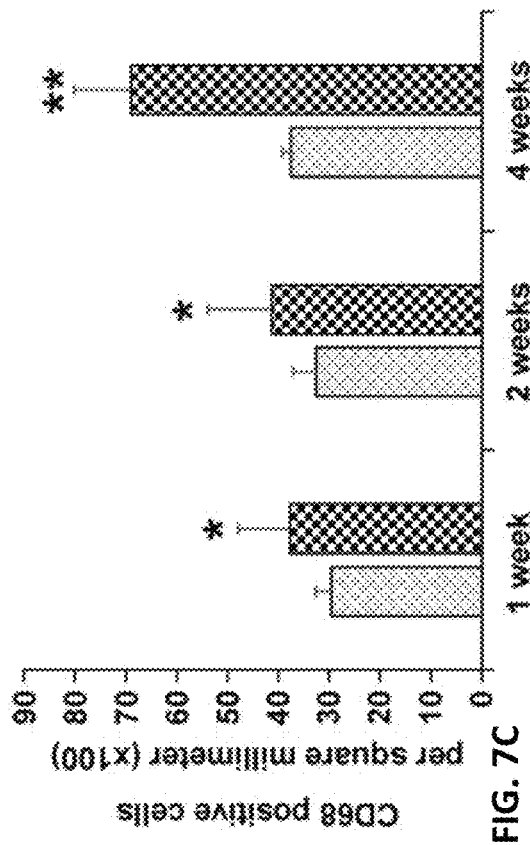
Figure 8:
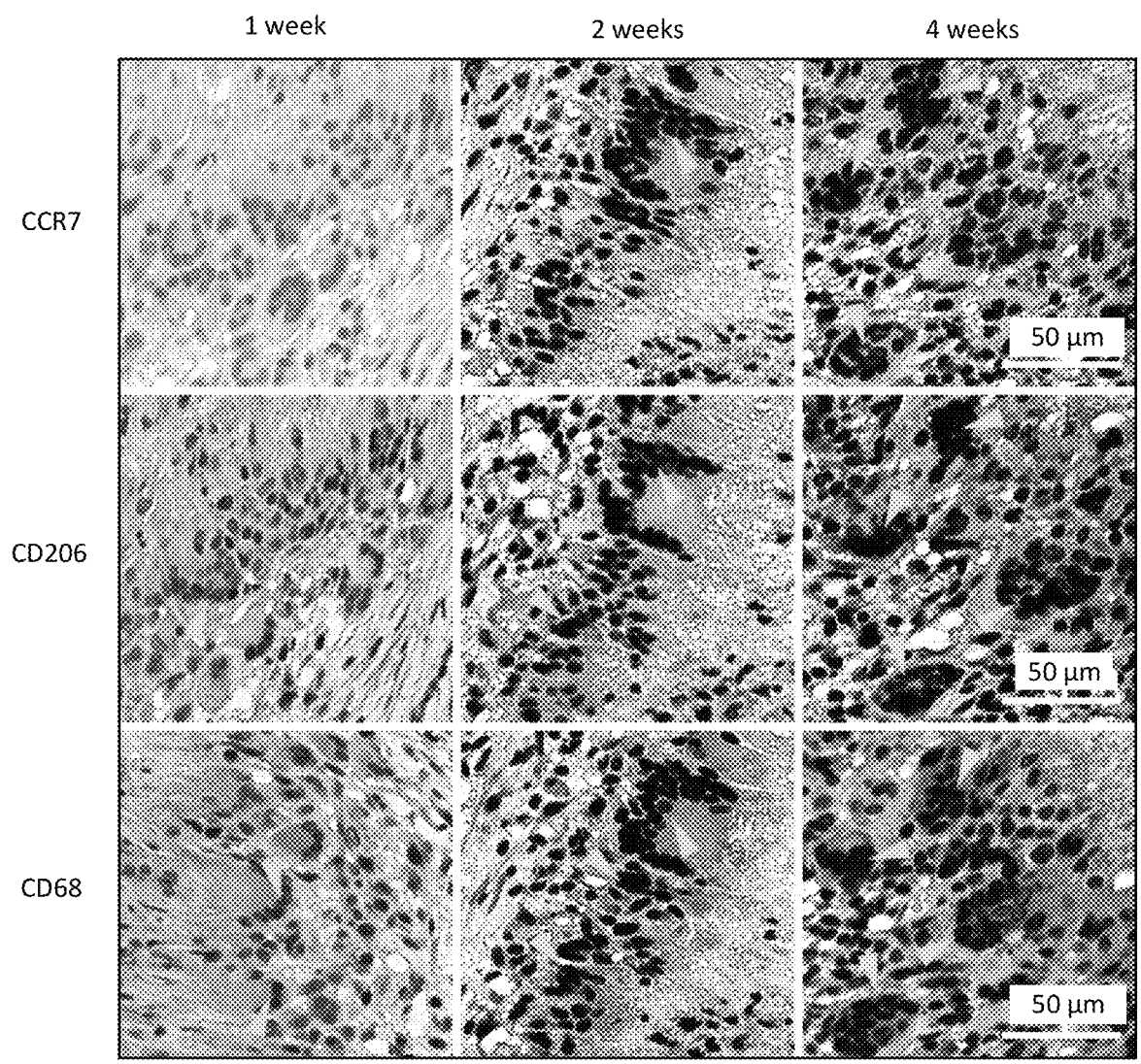
FIG. 8 shows multinucleated giant cells after subcutaneous implantation of 3D expanded nanofiber scaffolds with punched holes. The rats were scarified at week 1, 2, and 4 after surgery. The multinucleated giant cells were stained against CD68—a surface marker for pan macrophages, CD 206—a surface marker for macrophages in M2 phase, and CCR7—a surface marker for macrophages in M1 phase. Arrows indicate multinucleated giant cells.

Immunohistological staining of 3D nanofiber scaffolds with arrayed holes and the surrounding tissues was performed in order to identify the infiltrated macrophages with different surface makers (FIG. 6). The results indicated that the number of CCR7 positive cells (macrophages in M1 phase which encourage inflammation) decreased while the number of CD206 (macrophages in M2 phase which decrease inflammation and encourage tissue repair) and CD 68 (pan macrophages) positive cells increased with increasing the implantation time. The quantified data for macrophages with different surface markers was shown in FIG. 7, indicating a dramatic increase of M2/M1 ratio at week 4 after implantation. In contrast, M2/M1 ratios remained constant from week 1 to week 4 for traditional nanofiber mats (Jiang, et al. (2016) Adv. Healthcare Mater., 5:2993-3003). To reveal the expressing markers and spatiotemporal distributions of multinucleate giant cells, the highly magnified immunostaining images were analyzed with different surface markers (FIG. 8), indicating multinucleated giant cells were heterogeneous likely expressing CCR7, CD 206, and/or CD68 markers, which may be important for the new blood vessel formation and tissue regeneration (Barbeck, et al. (2016) J. Biomed. Mater. Res. Part A, 104:413-418). Therefore, it was confirmed that subcritical $CO_2$ fluid expanded 3D nanofiber scaffolds with arrayed holes promotes cellular infiltration, neovascularization, and positive host response.

Due to the biomimetic property, electrospun nanofibers have been widely used as scaffolds for regenerative medicine (Xie, et al. (2008) Macromol. Rapid Commun., 29:1775-1792). However, the traditional electrospinning often produce nanofiber membranes/mats with smaller pore size and tight structure, limiting cellular infiltration because of its intrinsic property (Jiang, et al. (2015) ACS Biomater. Sci. Eng., 1:991-1001). 3D electrospun nanofiber scaffolds have been developed making use of sacrificial templates (e.g., hydrophilic fibers, ice, and salts), manipulation of electrical field (e.g., customized collector and additive of ionic salts), noobing/weaving, melt jet writing/printing, and modified gas-foaming (Xie, et al. (2012) Adv. Healthcare Mater., 1:674-678; Hochleitner, et al. (2015) Biofabrication 7:035002). These methods are associated with various problems (e.g., time consuming, limited thickness, and necessitate the use of aqueous solution). In this study, a simple and novel approach to generate 3D nanofiber scaffolds via depressurization of subcritical $CO_2$ fluid is demonstrated. Based on the $CO_2$ phase diagram (Mazzoldi, et al. (2008) Int. J. Greenh. Gas Con., 2:210-218), the $CO_2$ liquid phase changes to the gas phase when the pressure is reduced rapidly. The $CO_2$ liquid that permeates fiber matrix changes into $CO_2$ gas bubbles and greatly expand the fiber matrix. After venting the $CO_2$ gas, the expanded nanofiber scaffolds can be readily formed without freeze-drying. For this expansion process, the plasma treatment procedure is also eliminated as $CO_2$ fluid easily penetrates the PCL nanofiber membranes, probably due to its non-polar property. Importantly, this method allows the expansion of nanofiber membranes in minutes. Compared with previous approaches, the method described herein saves time, eliminates the use of an aqueous solution and freeze-drying process, is environmentally friendly, uses low temperature processing, and maintains the aligned nanotopography. Importantly, nanofiber membranes made of water-soluble polymers (e.g., PVP) can be expanded into 3D scaffolds using the subcritical $CO_2$ fluid (FIG. 2), which was not possible in previous studies. Furthermore, this $CO_2$ expansion process can maintain the bioactivity of encapsulated molecules, which is critical as 3D nanofiber scaffolds often combine with growth factors or other bioactive molecules for use in regenerative medicine.

Figure 9:
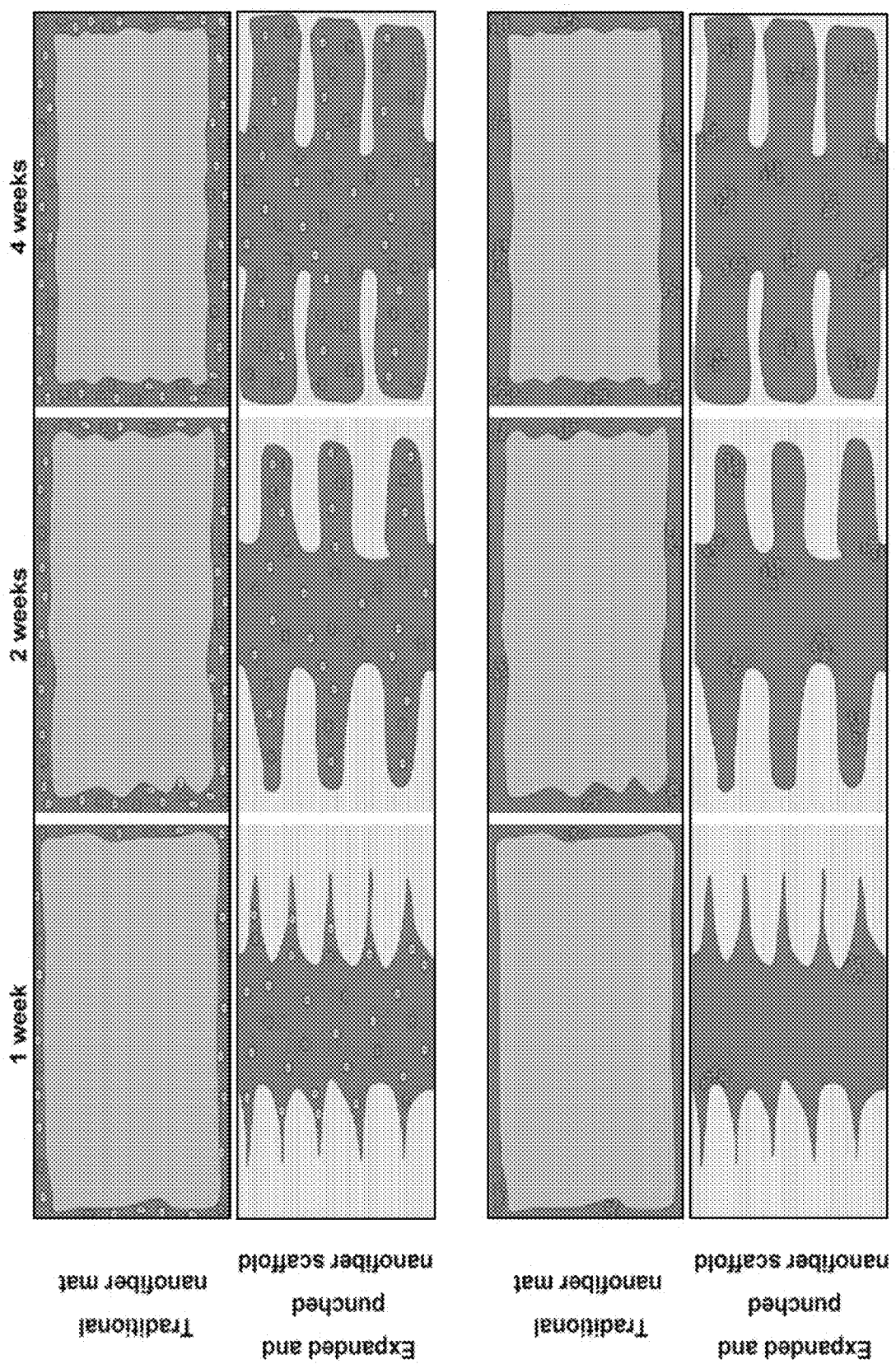
FIG. 9 provides a schematic illustrating the cell infiltration and spatiotemporal distributions of M1 macrophages (light grey), M2 macrophages (grey) (top panel) and multinucleated giant cells (bottom panel) on the surface of traditional nanofiber mats and within expanded 3D nanofiber scaffolds with arrayed holes after subcutaneous implantation. The cell-infiltrated area is labeled in dark grey.

Electrospun nanofiber membranes have been expanded in aqueous solutions using a modified gas-foaming technique. The resultant 3D scaffolds can facilitate cellular infiltration through the gaps between nanofiber layers. In this work, the 3D nanofiber scaffolds generated by subcritical $CO_2$ fluid showed a similar structure as the ones expanded in a $NaBH_4$ aqueous solution. Arrayed holes were generated throughout the scaffolds under a cryogenic condition for enhancement of cellular infiltration. Indeed, cells penetrated the scaffolds not only from sides but also from the holes (FIG. 5A). On the basis of immunostaining results, the cellular infiltration and spatiotemporal distributions of M1 macrophages, M2 macrophages, and multinucleated giant cells within the scaffold after implantation for 1, 2, and 4 weeks was determined, which are schematically illustrated in FIG. 9. For traditional nanofiber mats, cells often stay on the surface of nanofiber mats with marginal penetration and form collagen capsules (FIG. 9A). For $CO_2$ expanded 3D nanofiber scaffolds with arrayed holes, cells infiltrated into the punched holes within 1 week and continued penetrating to the scaffolds through the gaps between nanofiber layers. The infiltration of macrophages showed a similar trend. There were more M1 macrophages at week 1 and 2 but more M2 macrophages at week 4. At week 1, multinucleated giant cells were mostly located on the surface of punched holes. At week 2, some giant cells were formed either on the surface of punched holes or within the infiltrated fiber layers. At week 4, multinucleated giants cells were relatively evenly distributed throughout the infiltrated areas. In addition, the multinucleated giant cells show heterogeneous phenotypes with positive staining of different markers including CCR7, CD208 and CD68 (FIG. 6), indicating the importance for tissue regeneration. The $CO_2$ expanded nanofiber scaffolds described herein can be used for regeneration of specific tissues, in particular, those tissues with anisotropic properties such as nerve, muscle and tendon.

In conclusion, the transformation of electrospun nanofiber membranes from 2D to 3D has been demonstrated using the subcritical $CO_2$ fluid. This method provides several advantages over previous approaches such as shortening the processing time, eliminating the use of aqueous solutions and freeze-drying procedures, and avoiding the loss of encapsulated biologics. Most importantly, this method maintains the bioactivity of encapsulated molecules to a greater extent. Further, holes across nanofiber membranes can be generated through a micro-punch under a cryogenic condition to further promote cellular penetration and new blood vessel formation. These transformed 3D nanofiber scaffolds can be used in tissue repair/regeneration, engineering 3D tissue models, wound dressing, hemostasis, and topical drug delivery.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for producing an expanded nanofiber or microfiber structure with increased porosity and thickness, said method comprising exposing the nanofiber structure or microfiber structure to a subcritical fluid and depressurizing, wherein said depressurization increases the porosity and thickness of the nanofiber structure or microfiber structure.

2. The method of claim 1, wherein said subcritical fluid comprises $CO_2$, $N_2$, $N_2O$, hydrocarbons, or fluorocarbons.

3. The method of claim 1, wherein said subcritical fluid is subcritical $CO_2$.

4. The method of claim 1, wherein said exposure comprises immersing said nanofiber structure or microfiber structure in said subcritical fluid.

5. The method of claim 1, wherein said nanofiber or microfiber structure comprises electrospun fibers.

6. The method of claim 1, wherein said nanofiber or microfiber structure comprises a plurality of uniaxially-aligned nanofibers or microfibers, random nanofibers or microfibers, and/or entangled nanofibers or microfibers.

7. The method of claim 1, further comprising preparing said nanofiber structure or microfiber structure comprising a plurality of nanofibers or microfibers prior to said exposure to the subcritical fluid.

8. The method of claim 1, wherein said nanofibers or microfibers comprise hydrophilic polymers.

9. The method of claim 1, wherein said nanofibers or microfibers comprise hydrophobic polymers.

10. The method of claim 9, wherein said hydrophobic polymer is poly(caprolactone).

11. The method of claim 1, wherein said nanofiber structure or microfiber structure comprises an active agent.

12. The method of claim 11, wherein said active agent is selected from the group consisting of a therapeutic agent, a growth factor, a signaling molecule, a cytokine, a hemostatic agent, an antimicrobial, and an antibiotic.

13. The method of claim 11, wherein said active agent is added to the nanofiber structure or microfiber structure after said exposure to the subcritical fluid.

14. The method of claim 1, wherein the steps of i) exposing the nanofiber structure or microfiber structure to a subcritical fluid and ii) depressurizing, are performed more than once.

15. The method of claim 14, wherein the steps of i) exposing the nanofiber structure or microfiber structure to a subcritical fluid and ii) depressurizing, are repeated 1 to 5 times.

16. The method of claim 1, wherein said nanofiber or microfiber structure comprises an array of holes or wells.

17. The method of claim 1 further comprising crosslinking the nanofiber or microfiber structure.

18. The method of claim 16, wherein said array of holes or wells has between 1 and 200 holes or wells.

19. The method of claim 16, wherein each well or hole has a diameter of about 0.1 to about 5 mm.

20. The method of claim 1, further comprising inserting or punching an array of holes or wells into said nanofiber or microfiber structure prior to said exposure to a subcritical fluid and depressurizing.

* * * * *